United States Patent
Lee et al.

(10) Patent No.: US 10,617,758 B2
(45) Date of Patent: Apr. 14, 2020

(54) ANTI-CANCER VACCINE COMBINATION

(71) Applicants: Global BioPharma, Inc., Taipei (TW); Taipei Medical University, Taipei (TW)

(72) Inventors: Huei Lee, Taipei (TW); Yu-Ju Huang, Taipei (TW)

(73) Assignee: Global Biopharma, Inc., Taipei (TW)

( * ) Notice: Subject to any disclaimer, the term of this patent is extended or adjusted under 35 U.S.C. 154(b) by 0 days.

(21) Appl. No.: 15/766,459

(22) PCT Filed: Oct. 11, 2016

(86) PCT No.: PCT/US2016/056390
§ 371 (c)(1),
(2) Date: Apr. 6, 2018

(87) PCT Pub. No.: WO2017/062976
PCT Pub. Date: Apr. 13, 2017

(65) Prior Publication Data
US 2018/0280508 A1    Oct. 4, 2018

Related U.S. Application Data

(60) Provisional application No. 62/239,673, filed on Oct. 9, 2015.

(51) Int. Cl.
| | |
|---|---|
| C07K 16/28 | (2006.01) |
| A61K 39/00 | (2006.01) |
| A61K 39/395 | (2006.01) |
| C07K 16/30 | (2006.01) |
| G01N 33/574 | (2006.01) |
| A61K 39/42 | (2006.01) |
| A61K 39/12 | (2006.01) |
| A61P 35/04 | (2006.01) |
| A61K 38/16 | (2006.01) |
| A61K 45/06 | (2006.01) |
| A61P 31/14 | (2006.01) |

(52) U.S. Cl.
CPC ............ *A61K 39/42* (2013.01); *A61K 38/162* (2013.01); *A61K 39/12* (2013.01); *A61K 39/395* (2013.01); *A61K 39/39541* (2013.01); *A61K 45/06* (2013.01); *A61P 35/04* (2018.01); *A61K 2039/523* (2013.01); *A61K 2039/53* (2013.01); *A61K 2039/6037* (2013.01); *A61P 31/14* (2018.01); *C12N 2710/20034* (2013.01)

(58) Field of Classification Search
CPC ............ C07K 2317/76; C07K 2317/92; A61K 2300/00; A61K 39/39558; A61K 2039/505
See application file for complete search history.

(56) References Cited

FOREIGN PATENT DOCUMENTS

| WO | 2013181452 A1 | 12/2013 |
| WO | WO2015134722 | * 9/2015 |

OTHER PUBLICATIONS

OPDIVO (nivolumab) Package Insert, Bristol-Myers Squibb Company, 2015: pdf pp. 1-31.*
Carbognin et al., "Differential activity of nivolumab, pembrolizumab and MPDL3280A according to the tumor expression of programmed death-ligand-1 (PD-L1): sensitivity analysis of trials in melanoma, lung and genitourinary cancers," PLoS One, 2015, 10(6):1-16.*
Mkrtichyan et al. "Anti-PD-1 antibody significantly increases therapeutic efficacy of Listeria monocytogenes (Lm)-LLO immunotherapy," Journal for Immunotherapy of Cancer, 2013, 1(15): pdf pp. 1-9.*
Office Action in corresponding Taiwan application 104133408 dated Jan. 19, 2019, translation included, 8 pages.
Shasha Song et al, "Dendritic cells with an increased PD-L1 by TGF-β induce T cell anergy for the cytotoxicity of hepatocellular carcinoma cells", International Immunopharmacology, vol. 20, Issue 1, May 2014, 117-123.

* cited by examiner

*Primary Examiner* — Barry A Chestnut
(74) *Attorney, Agent, or Firm* — Duane Morris LLP

(57) ABSTRACT

The invention relates to an anti-cancer vaccine combination. Particularly, the invention relates to a pharmaceutical combination comprising a PD-L1/PD-1 expression inhibitor in combination with a viral antigen-associated vaccine.

18 Claims, 12 Drawing Sheets
Specification includes a Sequence Listing.

ANTI-CANCER VACCINE COMBINATION

CROSS-REFERENCE TO RELATED APPLICATIONS

This application is a § 371 national stage entry of International Application No. PCT/US2016/056390, filed Oct. 11, 2016, which claims priority to U.S. Provisional Application No. EP 62/239,673, filed Oct. 9, 2015, the entire contents of which are incorporated herein by reference.

FIELD OF THE INVENTION

The invention relates to an anti-cancer vaccine combination. Particularly, the invention relates to a pharmaceutical combination comprising a PD-L1/PD-1 expression inhibitor in combination with a viral antigen-associated vaccine.

BACKGROUND OF THE INVENTION

Programmed death-1 (PD-1) is a costimulatory molecule that provides an inhibitory signal in T cell activation. Program death ligand-1 (PD-L1) acts as an inhibitor of human T cell responses by binding to its receptor PD-1 to create the tumor microenvironment. This, in turn, results in tumor progression due to tumor immune surveillance. The PD-L1 protein is abundantly expressed in various human cancers, including non-small cell lung cancer (NSCLC). PD-L1-positive lung tumors show significantly lower numbers of tumor infiltrating lymphocytes (TILs) when compared to PD-L1-negative lung tumors, which suggests that PD-L1 expression in tumor cells may contribute to the negative regulation of the antitumor immune response in NSCLC. Furthermore, a high expression of PD-L1 may contribute to poor prognosis and tumor immune escape by suppressing the maturation of tumor infiltrating dendritic cells.

Poor prognosis in NSCLC is associated with the epithelial-mesenchymal transition (EMT), a key process that drives cancer metastasis. The EMT is highly associated with an inflammatory tumor microenvironment in NSCLC and immune activation that coexists with the elevation of multiple targetable immune checkpoint molecules, such as PD-L1. A further association is seen with the increases in tumor infiltration by CD4+Foxp3+ regulatory T cells that display an EMT phenotype. The PD-1/PD-L1 axis therefore plays a crucial role in tumor progression, the EMT, and poor prognosis in NSCLC.

Human papillomavirus (HPV) 16/18 infection is associated with lung cancer development. The HPV16/18 E6 oncoprotein promotes tumor growth and invasion by attenuating the expression of IL-10, TIMP-3, paxillin, and FOXM1. Tumor invasion induced by E6-mediation of these molecules occurs by triggering the EMT. We therefore speculated that the E6 oncoprotein might induce PD-L1 expression, which would induce tumor invasion and confer poor prognosis in NSCLC.

US20110177088 relates to a method of treatment of hematologic malignancies comprising the step of administering to a subject in need thereof a therapeutically effective amount of a ligand of PD1, wherein said ligand of PD1 is selected from the group consisting of PD-L1 or a fragment thereof which binds to PD1, PD-L2 or a fragment thereof which binds to PD1, and an anti-PD1 antibody or a fragment thereof which binds to PD1, and wherein the hematologic malignancy is selected from the group consisting of a chronic lymphocytic leukemia (CLL) of B-cell origin, a small lymphocytic lymphoma (SLL) of B-cell origin, a multiple myeloma, an acute B cell leukemia and a mantle cell lymphoma. US 20130149305 provides a soluble CD80 protein that interacts with programmed death ligand 1 (PD-L1) and thereby inhibiting the interaction of PD-L1 with T-cell expressed programmed death 1 (PD1) receptor, and thus, minimizing PD-L1 mediated immune suppression. The tumor-infiltrating T cells have been found to upregulate immunosuppressive pathways, such as PD-L1, in a paracrine fashion on tumor cells. Particularly, Vamsidhar Velcheti et al. indicates that PD-L1 expression was significantly associated with tumor-infiltrating lymphocytes and a study on patients with non-small cell lung cancer showed that greater PD-L1 protein and mRNA expression is associated with increased local lymphocytic infiltrate and longer survival (Vamsidhar Velcheti et al., *Programmed Death Ligand-1 Expression in Non-small Cell Lung Cancer, Laboratory Investigation* (2014) 94, 107-116).

Antibody-mediated blockade of PD-L1 can induce a durable tumor regression and prolonged stabilization of disease in patients with NSCLC. The preliminary data showed a positive correlation between the HPV16/18 E6 oncoprotein and PD-L1 expression in a small subset of NSCLC patients. An oncoprotein vaccine, the Lm-LLO-E7 vaccine, suppresses tumor growth in a TC-1 animal model. (Peng X, Hussain S F, Paterson Y. *The ability of two Listeria monocytogenes vaccines targeting human papillomavirus-16 E7 to induce an antitumor response correlates with myeloid dendritic cell function. Journal of immunology* 2004; 172:6030-8; Gunn G R, Zubair A, Peters C, Pan Z K, Wu T C, Paterson Y. *Two Listeria monocytogenes vaccine vectors that express different molecular forms of human papilloma virus*-16 (HPV-16) E7 *induce qualitatively different T cell immunity that correlates with their ability to induce regression of established tumors immortalized by HPV*-16. *Journal of immunology* 2001; 167:6471-9.)

However, there is a need to further develop a drug effective in immunotherapy.

SUMMARY OF THE INVENTION

The invention provides a pharmaceutical combination, comprising an anti-PD-L1 antibody or anti-PD-1 antibody in combination with a HPV antigen-associated vaccine.

In some embodiments, the anti-PD-L1 antibody is atezolizumab or MEDI4736. In some embodiments, the anti-PD-1 antibody is nivolumab or pembrolizumab. In some embodiments, the HPV-associated vaccine is a vector carrying Lm-LLO-E6 fusion protein. Preferably, the species of *Listeria* is *Listeria monocytogenes*.

The invention also provides a method for treating and/or preventing a tumor growth, invasion and/or metastasis in a subject suffering from a virus-associated tumor, comprising administering an anti-PD-L1 antibody or anti-PD-1 antibody and a HPV antigen-associated vaccine.

The invention also provides a method for improving a PD-1/PD-L1 cancer immunotherapy in a subject, comprising administering an anti-PD-L1 antibody or anti-PD-1 antibody in combination with a HPV antigen-associated vaccine.

In some embodiments, the anti-PD-L1 antibody or anti-PD-1 antibody is in a dosing amount ranging from about 0.1 mg/kg to about 30 mg/kg. In some embodiments, the HPV antigen-associated vaccine is in a dosing amount ranging from about $1 \times 10^4$ to about $1 \times 10^{12}$ CFU/dose.

In some embodiments, the HPV-associated cancer is lung cancer, cervical cancer, vagina cancer, vulva cancer, penis cancer, anus cancer, rectum cancer, and oropharynx cancer in one embodiment, the HPV-associated cancer is HPV-infected lung or cervical cancer. In one embodiment, the HPV-associated cancer is PD-L1-positive lung tumor. Preferably, the lung cancer is non-small cell lung cancer.

DETAILED DESCRIPTION OF THE INVENTION

Figure 1:
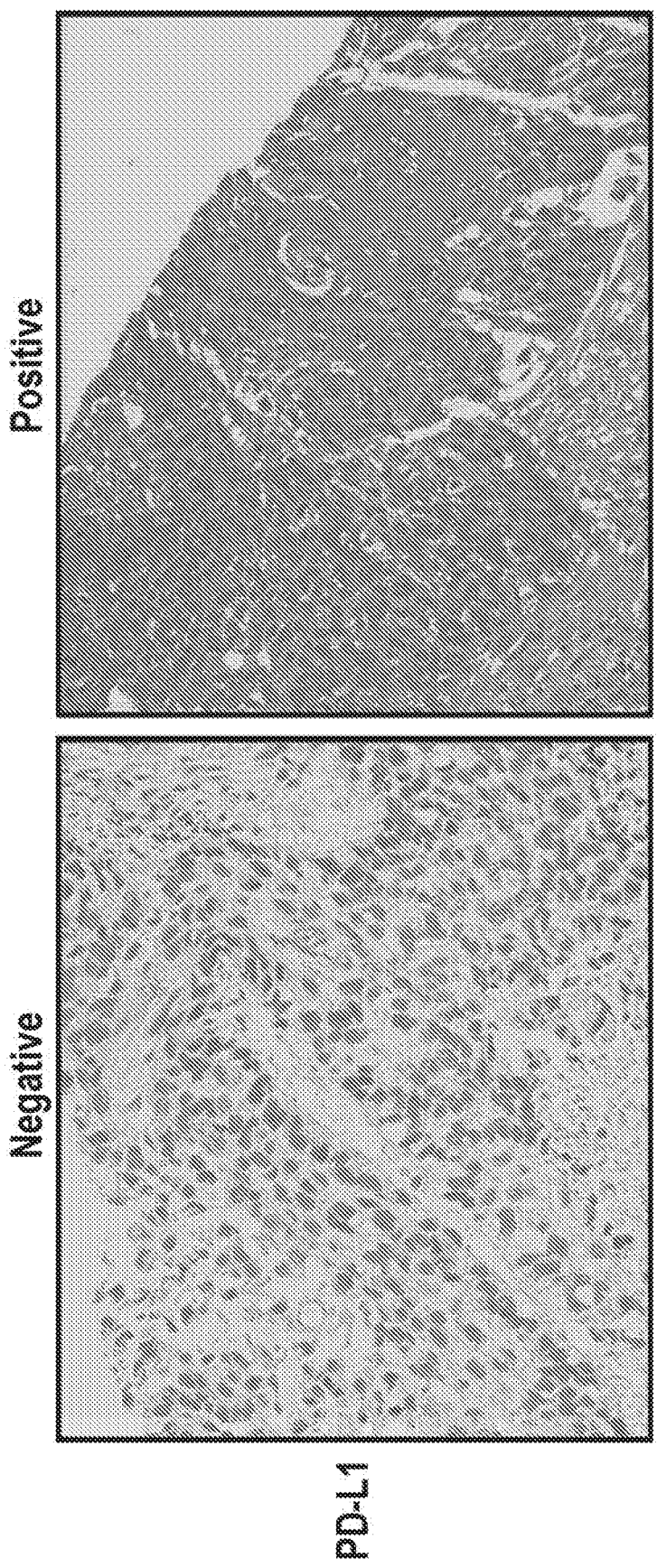
FIG. 1 shows the representative immunostaining results for PD-L1 expression in tumors from NSCLC patients.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. For example, the term "a cell" includes a plurality of cells, including mixtures thereof.

As used herein, the terms "tumor" and "cancer" are used interchangeably and refer to a malignant new growth of tissue that possesses no physiological function and arises from uncontrolled usually rapid cellular proliferation.

As used herein, a "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo.

As used herein, the term "pharmaceutically acceptable carrier", refers to encompasses any of the standard pharmaceutical carriers, e.g., a phosphate buffered saline solution, water, and emulsions, such as an oil/water or water/oil emulsion, and various types of wetting agents. The compositions may also include stabilizers and preservatives and any of the above noted carriers with the additional proviso that they be acceptable for use in vivo. For examples of carriers, stabilizers and adjuvants, see Martin REMINGTON'S PHARM. SCI., 18th Ed., Mack Publ. Co., Easton, Pa. (1995), and in the "PHYSICIAN'S DESK REFERENCE", 58th ed., Medical Economics, Montvale, N.J. (2004).

As used herein, the term "subject" is defined herein to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

As used herein, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or an antibody or dosage form provided herein, with or without one or more additional active agent(s), after the diagnosis or onset of symptoms of the particular disease.

As used herein, the term "antibody" is meant to include both intact molecules as well as fragments thereof that include the antigen-binding site. These include, but not limited to, Fab and F(ab')$_2$ fragments which lack the Fc fragment of an intact antibody, and a bi-specific antibody.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of a compound or an antibody or dosage form provided herein, with or without one or more other additional active agent(s), prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment.

As used herein, the term "relapsed" refers to a situation where a subject, that has had a remission of cancer after a therapy, has a return of cancer cells.

As used herein, the term "refractory" or "resistant" refers to a circumstance where a subject, even after intensive treatment, has residual cancer cells in the body.

As used herein, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to.

As used herein, the term "anticancer agent" or "cancer therapeutic agent" is meant to include anti-proliferative agents and chemotherapeutic agents.

As used herein, the terms "co-administration" and "in combination with" include the administration of two or more therapeutic agents simultaneously, concurrently, separately or sequentially within no specific time limits unless otherwise indicated. In one embodiment, the therapeutic agents are in the same composition or unit dosage form. In other embodiments, the therapeutic agents are in separate compositions or unit dosage forms.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients.

As used herein, the term "simultaneous" therapeutic use refers to the administration of at least two active ingredients by the same route and at the same time or at substantially the same time.

In one aspect, the invention provides a pharmaceutical combination, comprising an anti-PD-L1 antibody or anti-PD-1 antibody in combination with a HPV antigen-associated vaccine. In one embodiment, the combination comprises about 5 to about 50 mg/mL of the anti-PD-L1 antibody or anti-PD-1 antibody and about $1\times10^4$ to about $1\times10^{12}$ CFU/dose of the HPV antigen-associated vaccine.

In some embodiments, the anti-PD-L1 antibody or anti-PD-1 antibody in the combination is in an amount of about 5 mg to about 45 mg, about 5 mg to about 40 mg, about 5 mg to about 35 mg, about 5 mg to about 30 mg, about 10 mg to about 45 mg, about 10 mg to about 40 mg, about 10 mg to about 35 mg, about 10 mg to about 30 mg, about 15 mg to about 45 mg, about 15 mg to about 40 mg, about 15 mg to about 35 mg, about 15 mg to about 30 mg, about 20 mg to about 45 mg, about 20 mg to about 40 mg, about 20 mg to about 35 mg or about 20 mg to about 30 mg.

In some embodiments, the HPV antigen-associated vaccine in the combination is in an amount of about $1\times10^5$ to about $1\times10^{12}$ CFU/dose, about $1\times10^6$ to about $1\times10^{12}$ CFU/dose, about $1\times10^7$ to about $1\times10^{12}$ CFU/dose, about $1\times10^8$ to about $1\times10^{12}$ CFU/dose, about $1\times10^6$ to about $1\times10^{11}$ CFU/dose, about $1\times10^6$ to about $1\times10^{10}$ CFU/dose, about $1\times10^7$ to about $1\times10^{11}$ CFU/dose, about $1\times10^7$ to about $1\times10^{10}$ CFU/dose, about $1\times10^8$ to about $1\times10^{11}$ CFU/dose or about $1\times10^8$ to about $1\times10^{10}$ CFU/dose.

In another aspect, the invention provides a method for treating and/or preventing a tumor growth, invasion and/or metastasis in a subject suffering from a HPV-associated tumor, comprising administering an anti-PD-L1 antibody or anti-PD-1 antibody and a HPV antigen-associated vaccine. In one embodiment, the anti-PD-L1 antibody or anti-PD-1 antibody and a HPV antigen-associated vaccine can be administered simultaneously, concurrently, separately or sequentially. In one embodiment, the tumor is a HPV-associated tumor.

In another aspect, the invention provides a method for improving a PD-1/PD-L1 cancer immunotherapy in a subject, comprising administering an anti-PD-L1 antibody or anti-PD-1 antibody in combination with a HPV antigen-associated vaccine. In one embodiment, the anti-PD-L1 antibody or anti-PD-1 antibody and a HPV antigen-associated vaccine can be administered simultaneously, concurrently, separately or sequentially.

In one embodiment, the method can improve the prognosis of a cancer.

In some embodiments, the HPV-associated tumor is lung tumor, cervical tumor, vagina tumor, vulva tumor, penis tumor, anus tumor, rectum tumor, melanoma, non-small cell lung cancer (NSCLC), head and neck squamous cell carcinoma (HNSCC) and oropharynx tumor. In one embodiment, the HPV-associated tumor is HPV-infected lung or cervical tumor. In one embodiment, the HPV-associated tumor is PD-L1-positive lung tumor. Preferably, the lung cancer is non-small cell lung tumor.

In one embodiment, the anti-PD-L1 antibody is atezolizumab or MEDI4736. In one embodiment, the anti-PD-1 antibody is nivolumab or pembrolizumab.

In one embodiment, the HPV-associated vaccine is a therapeutic HPV-associated vaccine. In one embodiment, the HPV-associated vaccine is a vector carrying Lm-LLO-E6 fusion protein. Preferably, the vector carrying Lm-LLO-E6 fusion protein is a *Listeria* carrying plasmid expressing Lm-LLO-E6 fusion protein. Preferably, the species of *Listeria* is *Listeria monocytogenes*.

The nucleic acid sequence and amino acid sequence of Lm-LLO-E6 fusion protein are as follows.

DNA (1803 bp)

(SEQ ID NO: 1)
ATGAAAAAAATAATGCTAGTTTTTATTACACTTATATTAGTTAGTCTACC

AATTGCGCAACAAACTGAAGCAAAGGATGCATCTGCATTCAATAAAGAAA

ATTCAATTTCATCCATGGCACCACCAGCATCTCCGCCTGCAAGTCCTAAG

ACGCCAATCGAAAAGAAACACGCGGATGAAATCGATAAGTATATACAAGG

ATTGGATTACAATAAAAACAATGTATTAGTATACCACGGAGATGCAGTGA

CAAATGTGCCGCCAAGAAAAGGTTACAAAGATGGAAATGAATATATTGTT

GTGGAGAAAAAGAAGAAATCCATCAATCAAAATAATGCAGACATTCAAGT

TGTGAATGCAATTTCGAGCCTAACCTATCCAGGTGCTCTCGTAAAAGCGA

-continued

```
ATTCGGAATTAGTAGAAAATCAACCAGATGTTCTCCCTGTAAAACGTGAT

TCATTAACACTCAGCATTGATTTGCCAGGTATGACTAATCAAGACAATAA

AATAGTTGTAAAAAATGCCACTAAATCAAACGTTAACAACGCAGTAAATA

CATTAGTGGAAAGATGGAATGAAAAATATGCTCAAGCTTATCCAAATGTA

AGTGCAAAAATTGATTATGATGACGAAATGGCTTACAGTGAATCACAATT

AATTGCGAAATTTGGTACAGCATTTAAAGCTGTAAATAATAGCTTGAATG

TAAACTTCGGCGCAATCAGTGAAGGGAAAATGCAAGAAGAAGTCATTAGT

TTTAAACAAATTTACTATAACGTGAATGTTAATGAACCTACAAGACCTTC

CAGATTTTTCGGCAAAGCTGTTACTAAAGAGCAGTTGCAAGCGCTTGGAG

TGAATGCAGAAAATCCTCCTGCATATATCTCAAGTGTGGCGTATGGCCGT

CAAGTTTATTTGAAATTATCAACTAATTCCCATAGTACTAAAGTAAAAGC

TGCTTTTGATGCTGCCGTAAGCGGAAAATCTGTCTCAGGTGATGTAGAAC

TAACAAATATCATCAAAAATTCTTCCTTCAAAGCCGTAATTTACGGAGGT

TCCGCAAAAGATGAAGTTCAAATCATCGACGGCAACCTCGGAGACTTACG

CGATATTTTGAAAAAAGGCGCTACTTTTAATCGAGAAACACCAGGAGTTC

CCATTGCTTATACAACAAACTTCCTAAAAGACAATGAATTAGCTGTTATT

AAAAACAACTCAGAATATATTGAAACAACTTCAAAAGCTTATACAGATGG

AAAAATTAACATCGATCACTCTGGAGGATACGTTGCTCAATTCAACATTT

CTTGGGATGAAGTAAATTATGATCTCGAGCACCAAAAGAGAACTGCAAT

GTTTCAGGACCCACAGGAGCGACCCAGAAAGTTACCACAGTTATGCACAG

AGCTGCAAACAACTATACATGATATAATATTAGAATGTGTGTACTGCAAG

CAACAGTTACTGCGACGTGAGGTATATGACTTTGCTTTTCGGGATTTATG

CATAGTATATAGAGATGGGAATCCATATGCTGTATGTGATAAATGTTTAA

AGTTTTATTCTAAAATTAGTGAGTATAGACATTATTGTTATAGTTTGTAT

GGAACAACATTAGAACAGCAATACAACAAACCGTTGTGTGATTTGTTAAT

TAGGTGTATTAACTGTCAAAAGCCACTGTGTCCTGAAGAAAAGCAAAGAC

ATCTGGACAAAAGCAAAGATTCCATAATATAAGGGGTCGGTGGACCGGT

CGATGTATGTCTTGTTGCAGATCATCAAGAACACGTAGAGAAACCCAGCT

GTAA
```

Protein (601 aa)

(SEQ ID NO: 2)
```
MKKIMLVFITLILVSLPIAQQTEAKDASAFNKENSISSMAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYPNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYDLEHQKRTA

MFQDPQERPRKLPQLCTELQTTIHDIILECVYCKQQLLRREVYDFAFRDL

CIVYRDGNPYAVCDKCLKFYSKISEYRHYCYSLYGTTLEQQYNKPLCDLL

IRCINCQKPLCPEEKQRHLDKKQRFHNIRGRWTGRCMSCCRSSRTRRETQ

L*
```

In one embodiment, the subject is a relapsed or refractory subject. In one embodiment, the subject is a mammal. Preferably, the subject is a primate (e.g., human), a cow, a sheep, a goat, a horse, a dog, a cat, a rabbit, a rat or a mouse.

In one embodiment, the anti-PD-L1 antibody or anti-PD-1 antibody is in a dosing amount ranging from about 0.01 mg/kg to about 20 mg/kg. Preferably, the amount of the anti-PD-L1 antibody or anti-PD-1 antibody is about 0.01 mg/kg to about 15 mg/kg, about 0.01 mg/kg to about 10 mg/kg, about 0.01 mg/kg to about 5 mg/kg, about 0.01 mg/kg to about 1 mg/kg, about 0.05 mg/kg to about 20 mg/kg, about 0.05 mg/kg to about 15 mg/kg, about 0.05 mg/kg to about 10 mg/kg, about 0.05 mg/kg to about 5 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.5 mg/kg to about 20 mg/kg, about 0.5 mg/kg to about 15 mg/kg, about 0.5 mg/kg to about 10 mg/kg, about 0.5 mg/kg to about 5 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 20 mg/kg, about 5 mg/kg to about 15 mg/kg, about 5 mg/kg to about 10 mg/kg, about 5 mg/kg to about 5 mg/kg, about 5 mg/kg to about 10 mg/kg, about 10 mg/kg to about 20 mg/kg, or about 10 mg/kg to about 15 mg/kg.

In one embodiment, the HPV antigen-associated vaccine is in a dosing amount ranging from about $1\times10^4$ to about $1\times10^{12}$ CFU/dose, about $1\times10^5$ to about $1\times10^{12}$ CFU/dose, about $1\times10^6$ to about $1\times10^{12}$ CFU/dose, about $1\times10^7$ to about $1\times10^{12}$ CFU/dose, about $1\times10^8$ to about $1\times10^{12}$ CFU/dose, about $1\times10^6$ to about $1\times10^{11}$ CFU/dose, about $1\times10^6$ to about $1\times10^{10}$ CFU/dose, about $1\times10^7$ to about $1\times10^{11}$ CFU/dose, about $1\times10^7$ to about $1\times10^{10}$ CFU/dose, about $1\times10^8$ to about $1\times10^{11}$ CFU/dose or about $1\times10^8$ to about $1\times10^{10}$ CFU/dose.

The pharmaceutical combinations of the present invention may further comprise one or more pharmaceutically acceptable carriers, excipients, and other agents that are incorporated into formulations to provide improved transfer, delivery, tolerance, and the like (herein collectively referred to as "pharmaceutically acceptable carriers or diluents"). A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, J Pharm Sci Technol 52:238-311.

Accordingly, combinations/compositions designed for oral, lingual, sublingual, buccal and extrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like.

Preferably, the combinations/compositions of the present invention is administered parenterally such as, for example, by intravenous, intramuscular, intrathecal or subcutaneous injection, intranasally, vaginally, rectally, lingually, sublingually, buccally, intrabuccaly and transdermally to the patient. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampoules, disposable syringes or multiple dose vials made of glass or plastic.

Rectal administration includes administering the pharmaceutical combinations/compositions into the rectum or large intestine. This can be accomplished using suppositories or enemas. Suppository formulations can easily be made by methods known in the art. For example, suppository formulations can be prepared by heating glycerin to about 120° C., dissolving the pectin composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

One embodiment of the invention shows that a combination comprising an anti-PD-L1 antibody or anti-PD-1 antibody in combination with a HPV antigen-associated vaccine may be an efficient treatment for suppression of tumor growth and metastasis induced by HPV-infected lung and cervical cancer cells.

EXAMPLES

Materials and Methods

The Lm-LLO, LLO-E6 and Lm-LLO-E7 used in the following examples refer to Peng X, Hussain S F, Paterson Y. The ability of two Listeria monocytogenes vaccines targeting human papillomavirus-16 E7 to induce an antitumor response correlates with myeloid dendritic cell function. Journal of immunology 2004; 172:6030-8; and Gunn G R, Zubair A, Peters C, Pan Z K, Wu T C, Paterson Y. Two Listeria monocytogenes vaccine vectors that express different molecular forms of human papilloma virus-16 (HPV-16) E7 induce qualitatively different T cell immunity that correlates with their ability to induce regression of established tumors immortalized by HPV-16. Journal of immunology 2001; 167:6471-9. The anti-PD-L1 antibody used in the following examples is that in BioLegend Cat #329716, RRID:AB_11149168.

Study Subjects

Lung tumor specimens were collected from 122 patients who underwent primary NSCLC surgical resection at the Department of Thoracic Surgery, Taichung Veterans General Hospital (Taichung, Taiwan) between 1998 and 2004. Patients were asked to submit written informed consent; the study was approved by the Institutional Review Board (TMUH No. 201301051). The tumor type and stage of each collected specimen were histologically determined in accordance with the World Health Organization classification system. Cancer relapse data were obtained from chart review and confirmed by thoracic surgeons. Clinical parameters and OS and RFS data were collected from chart review and the Taiwan Cancer Registry, Department of Health, Executive Yuan, ROC.

Cell Lines

TL-1 and TL-4 cells were kindly provided by Dr. Y.-W. Cheng (Graduate Institute of Cancer Biology and Drug Discovery, Taipei Medical University, Taipei, Taiwan) (10). SiHa and C33A cells were obtained from the Bioresource Collection and Research Center, the Food Industry Research and Development Institute (Hsinchu, Taiwan). TL-1, TL-4, and C33A cancer cell lines were maintained in RPMI-1640 medium (HyClone, Logan, Utah). SiHa cancer cell lines were maintained in DMEM medium (HyClone, Logan, Utah). The media contained 10% fetal bovine serum (FBS) supplemented with penicillin (100 U/mL) and streptomycin (100 mg/mL). The cells were cultured according to the suppliers' instructions. Once resuscitated, the cell lines were routinely authenticated (once every 6 months; the cells were last tested in December 2012) by cell morphology monitoring, growth curve analysis, species verification via isoenzymology and karyotyping, identity verification via short tandem repeat profiling analysis, and contamination checks.

Immunohistochemistry Analysis

Immunohistochemistry was performed to evaluate PD-L1 protein expression. Formalin-fixed and paraffin-embedded specimens were cut into 3 μm sections, mounted on glass, and dried overnight at 37° C. All sections were then deparaffinized in xylene, rehydrated through alcohol, and washed in phosphate-buffered saline. This buffer was used for all subsequent washes. Sections were heated in a microwave oven twice for 5 min in citrate buffer (pH 6.0) and then incubated for 60 min at room temperature following a conventional streptavidin peroxidase method (LSAB Kit K675, DAKO, Carpinteria, Calif.). Signals were developed with 3, 3'-diaminobenzidine for 5 min and the sections were counterstained with hematoxylin. Negative controls were obtained by leaving out the primary antibody. The intensities of signals were evaluated independently by three observers.

Plasmid Construction, Transfection, and Stable Clone Selection

The HPV 16 E6 cDNA plasmid and HPV 16 E6 small hairpin (sh)RNA were described previously. The PD-L1 cDNA plasmid was purchased from Addgene (Addgene Company, Cambridge, Mass.). The PD-L1 shRNA was obtained from the National RNAi Core Facility, Academia Sinica (Taipei, Taiwan). The target sequences for shRNA are presented in Supplementary Table 2. Nonspecific shRNA with a scrambled sequence and an empty vector expression were used as the controls in the knockdown and ectopic expressing experiments, respectively. The transfection and stable clone selection procedures have been described previously.

Anchorage Independent Soft-Agar Colony Formation

Anchorage independent growth was assayed as the ability of cells to form colonies on soft agar plates. The bottom agar consisted of growth medium containing 10% fetal bovine serum and 0.5% agarose in 6-well plates. A total of 300 cells was re-suspended in growth medium containing 10% fetal bovine serum and 0.4% agarose and placed on top of the bottom agar. The cells were grown at 37° C. in a humidified incubator in 5% $CO_2$. Colonies were visualized and quantified with a microscope after 14 days of cultivation, and the colonies larger than 100 µm in diameter were counted.

The Subcutaneous Animal Model

Six- to eight-week-old female BALB/c nude mice and C57Bl/6 mice were purchased from National Laboratory Animal Center (Taipei, Taiwan). Mice were cared for under protocols approved by the NLAC Animal Care and Use Committee. Lm-LLO-E6 (E6) vaccine and Lm-LLO-E7 (E7) vaccine were injected intraperitoneally at doses of $5 \times 10^6$ CFU/mouse. The anti-PD-L1 mAb obtained from BioLegend (San Diego, Calif.) was injected intravenously at a dose of 25 µg/mouse. The aim of the experiment was to determine the tumor growth changes induced by different treatments when compared with the control group. Briefly, mice were subcutaneously implanted with 500,000 TL-1 cells/mouse in the right flank on day 0. On day 7 (tumor size ~3-4 mm in diameter), the mice were injected with Lm-LLO-E6 or Lm-LLO-E7 intraperitoneally and/or with anti-PD-L1 mAb intravenously. Mice were treated with anti-PD-L1 mAb an additional three times, on days 14, 21, and 28 after tumor implantation. The control group of mice was only injected with TL-1 or SiHa cells. Tumors were measured every 3-4 days using digital calipers, and tumor volume was calculated using the formula $V=(W2 \times L)/2$, where V is volume, L is length (longer diameter), and W is width (shorter diameter). A flow chart is presented in Supplementary FIG. 1.

The Tail-Vein Metastatic Lung Tumor Animal Model

Lm-LLO-E6 (E6) and Lm-LLO-E7 (E7) vaccines were injected intraperitoneally at a dose of $5 \times 10^6$ CFU/mouse. The anti-PD-L1 mAb was injected intravenously at a dose of 25 µg/mouse. The aim of the experiment was to determine the changes in tumor growth and survival induced by the different treatments. Briefly, mice were injected with 100,000 TL-1 or SiHa cells/mouse by tail-vein injection on day 0. On day 14, the mice were injected with Lm-LLO-E6 or Lm-LLO-E7 vaccine intraperitoneally and/or with anti-PD-L1 mAb intravenously. Mice were treated with anti-PD-L1 mAb an additional three times, on days 21, 28, 35 after tumor cell injections. Mice continued to eat normally until death.

Statistical Analysis

All statistical analyses were conducted using the SPSS statistical software program, as described previously (version 17.0; SPSS, Inc., Chicago, Ill.) (18,19). A two-sided analysis of the variance in the statistical tests was conducted, and P values<0.050 were considered statistically significant.

Example 1

Therapeutic Experiment of Anti-PD-L1 Antibody and/or Combined With Lm-LLO-E6 Vaccine in Tumors 1. Development of Lm-LLO-E6 Vaccine.

The Listeria strains used in the E6 tumor Ag studies are Lm-LLO-E6 (hly-E6 fusion gene in an episomal expression system), Lm-E6 (single-copy E6 gene cassette integrated into Listeria genome), Lm-LLO-NP (hly-NP fusion gene in an episomal expression system), and Lm-Gag (single-copy HIV-1 Gag gene cassette integrated into the chromosome). Lm-LLO-NP, also known as DP-L2028 (Chen C J, Hsu L S, Lin L S, Lin S H, Chen M K, Wang H K, Hsu J D, Lee H, Yeh K T (2012) *Loss of nuclear expression of Kruppel-like factor 4 is associated with poor prognosis in patients with oral cancer. Human Pathology,* 43, 1119-1125), and Lm-Gag, also known as ZY-18 (Wang Y C, Sung W W, Wu T C, Wang L, Chien W P, Cheng Y W, Chen C Y, Shieh S H and Lee H* (2012). *Interleukin*-10 *haplotype may predict survival and relapse in resected non-small cell lung cancer. PLOS ONE,* 7, 7, e39525), have been previously described. E6 was amplified by PCR using the primers 5'-GGCTC-GAGCATGGAGATACACC-3' (SEQ ID NO: 6) (XhoI site is underlined) and 5'-GGGGACTAGTTTATGGTTTCT-GAGAACA-3' (SEQ ID NO: 7) (SpeI site is underlined) and ligated into pCR2.1 (Invitrogen, San Diego, Calif.). E6 was excised from pCR2.1 by double digest with XhoI and SpeI and ligated into pGG-55. The expression system, pGG-55, is modeled on pDP-2028 (Chen C J, Hsu L S, Lin L S, Lin S H, Chen M K, Wang H K, Hsu J D, Lee H, Yeh K T (2012). *Loss of nuclear expression of Kruppel-like factor 4 is associated with poor prognosis in patients with oral cancer. Human Pathology,* 43, 1119-1125). The hly-E6 fusion gene and prfA are cloned into pAM401, a multicopy shuttle plasmid, generating pGG-55. The hly promoter drives the expression of the first 441 aa of the hly gene product, LLO, which is joined by the XhoI site to the E6 gene. The result is a hly-E6 fusion gene that is transcribed and secreted as LLO-E6. By deleting the hemolytic C-terminus of LLO we have removed the hemolytic activity in the fusion protein. The pluripotential transcription factor, prfA, is also included on pGG-55. By transforming a prfA negative strain of Listeria, XFL-7 (a kind gift from Dr. Hao Shen, University of Pennsylvania), with pGG-55 we select for the retention of the plasmid in vivo. The hly promoter and gene fragment were generated using primers 5'-GGG GGC TAG CCC TCC TTT GAT TAG TAT ATT C-3' (SEQ ID NO: 8) (NheI site is underlined) and 5'-CTC CCT CGA GAT CAT AAT TTA CTT CAT C-3' (SEQ ID NO: 9) (XhoI site is underlined). The prfA gene was PCR amplified using primers 5'-GAC TAC AAG GAC GAT GAC CGA CAA GTG ATA ACC CGG GAT CTA AAT AAA TCC GTT T-3' (SEQ ID NO: 10) (XbaI site is underlined) and 5'-CCC GTC GAC AG CTC TTC TTG GTG AAG-3' (SEQ ID NO: 11) (SalI site is underlined). Lm-E6 was generated by introducing an expression cassette containing the hly promoter and signal sequence driving the expression and secretion of E6 into the orfZ domain of the *L. monocytogenes* genome. E6 was amplified by PCR using the primers 5'-GCG GAT CCC ATG GAG ATA CAC CTA C-3' (SEQ ID NO: 12) (BamHI site is underlined) and 5'-GCT CTA GAT TAT GGT TTC TGA G-3' (SEQ ID NO: 13) (XbaI site is underlined). E6 was then ligated into the pZY-21 shuttle vector. The resulting plasmid, pZY-21-E6, is an expression system that includes the previously described expression cassette inserted in the middle of a 1.6-kb sequence that corresponds to the orf X, Y, Z domain of the *L. monocytogenes* genome. *L. monocytogenes* strain 10403S was transformed with pZY-21-E6. The homology domain allows for insertion of the E6 gene cassette into the orfZ domain by homologous recombination. Clones were screened for integration of the E6 gene cassette into the orfZ domain. Bacteria were grown in brain heart infusion medium with (Lm-LLO-E6 and Lm-LLO-NP) or without (Lm-E6 and ZY-18) chloramphenicol (20 μg/ml). Bacteria were frozen in aliquots at −80° C.

2. Effects of Lm-LLO-E6 Vaccine on Established Tumor Growth

Six to eight weeks old female BALB/c nude mice and C57Bl/6 mice were purchased from National Laboratory Animal Center (Taipei, Taiwan). Mice were cared for under protocols approved by the NLAC Animal Care and Use Committee. TL1 cells were kindly provided by Dr. Cheng Y W. TC-1 cells that were derived by co-transfection of human papillomavirus strain 16 (HPV16) early proteins 6 and 7 (E6 and E7) and activated ras oncogene to primary C57BL/6 mouse lung epithelial cells were obtained from ATCC (Manassas, Va.), and cells were grown in RPMI 1640 supplemented with 10% FBS, penicillin and streptomycin (100 U/ml each) and L-glutamine (2 mM) at 37° C. with 5% $CO_2$. Listeria vaccine vectors with or without human papilloma virus-16 (HPV-16) E6 and E7 (Lm-LLO, LLO-E6 and Lm-LLO-E7) provided by Advaxis Inc. Both Lm-LLO, LLO-E6 and Lm-LLO-E7 were injected intraperitonealy at $5 \times 10^6$ CFU/mouse dose. The anti-PD-L1 and anti-PD-1 monoclonal antibody was obtained from CureTech (Israel) and was injected intravenously at a dose of 50 μg/mouse. All fluorescently labeled antibodies and appropriate isotype controls used for flow cytometry were purchased from BD Biosciences (San Jose, Calif.). The therapeutic experiments aimed to analyze tumor growth and survival were performed as described earlier. Briefly, C57Bl/6 mice were implanted with TC-1 cells and BALB/c nude were implanted with TL-1 cells with 500,000 cells/mouse subcutaneous in the right flank on day 0. On day 8 (tumor size ~3-4 mm in diameter), animals from appropriate groups (5 mice per group) were injected intraperitonealy with Lm-LLO or Lm-LLO-E6 or Lm-LLO-E7 with or without anti-PD-L1 or ant-PD-1 antibody intravenously. Mice were treated with vaccine and monoclonal antibody one more time on day 15 after tumor implantation. Another group of mice remained non-treated. Tumors were measured every 3-4 days using digital calipers, and tumor volume was calculated using the formula $V=(W^2 \times L)/2$, whereby V is volume, L is length (longer diameter) and W is width (shorter diameter).

Example 2

The Therapeutic Experiment of Anti-PD-L1 or Anti-PD-1 Monoclonal Antibody and/or Combined With Lm-LLO or Lm-LLO-E6 or Lm-LLO-E7 Vaccine in Metastatic Tumors 1. The Therapeutic Experiment of Anti-PD-L1 (BioLegend Cat #329716, RRID:AB_11149168) or Anti-PD-1 Monoclonal Antibody and/or Combined With Lm-LLO-E6 or -E7 Vaccine in TC-1-Induced Metastatic Lung Tumors Formation.

Six to eight weeks old female BALB/c nude mice and C57Bl/6 mice were purchased from National Laboratory Animal Center (Taipei, Taiwan). Mice were cared for under protocols approved by the NLAC Animal Care and Use Committee. Listeria vaccine vectors with or without human papilloma virus-16 (HPV-16) E6 and E7 (Lm-LLO, Lm-LLO-E6 and Lm-LLO-E7) were provided by Advaxis Inc. Lm-LLO, Lm-LLO-E6 and Lm-LLO-E7 were injected intraperitonealy at $5 \times 10^6$ CFU/mouse dose. The anti-PD-L1 and anti-PD-1 monoclonal antibody were obtained from BioLegend (Cat #329716, 329926) and were injected intravenously at dose of 0.1 mg/kg-30 mg/kg, respectively. All fluorescently labeled antibodies and appropriate isotype controls used for flow cytometry were purchased from BD Biosciences (San Jose, Calif.). The therapeutic experiments aimed to analyze tumor growth and survival were performed as described earlier (ref). Briefly, mice were implanted with 500,000 TC-1 cells/mouse subcutaneous in the right flank on day 0. On day 8 (tumor size ~3-4 mm in diameter), animals from appropriate groups (5 mice per group) were injected intraperitonealy with Lm-LLO or Lm-LLO-E6 or Lm-LLO-E7 and with or without anti-PD-L1 or anti-PD-1 antibody intravenously. Mice were treated with Lm-LLO or Lm-LLO-E6 or Lm-LLO-E7 vaccine and anti-PD-L1 or anti-PD-1 antibody one more time on day 15 after tumor implantation. Another group of mice remained non-treated. Tumors were measured every 3-4 days using digital calipers, and tumor volume was calculated using the formula $V=(W^2 \times L)/2$, whereby V is volume, L is length (longer diameter) and W is width (shorter diameter). In the groups of m-LLO, LLO-E6 or Lm-LLO-E7 in combination with the anti-PD-L1 or anti-PD-1 antibody, the tumors volumes almost reduces 100%, while in the anti-PD-L1 alone group, the tumor volume reduces around 10%.

2. Mouse Dendritic Cell Isolation, Purification and Analysis of PD-L1 Expression Mouse dendritic cells (DC) were isolated and purified from bone marrow as we described earlier. To obtain human DC, monocytes were isolated from healthy adult blood donors (National Institute of Health, Blood bank). Briefly, peripheral blood mononuclear cells (PBMC) were isolated from gradient centrifugation using Ficoll-Paque Plus (Amersham Biosciences) and, after washing, allowed to adhere to tissue culture plates for 2 h at 37° C. Non-adherent cells were removed by washing, and the adherent monocytes were cultured in a plate at 37° C., 5% $CO_2$ in complete RPMI 1640 consisting of RPMI 1640, 2 mM L-glutamine, penicillin (100 U/ml), streptomycin (100 ug/ml), 10 mM HEPES, 10% fetal bovine serum, 10 mM nonessential amino acids, 1 mM sodium pyruvate, and $5 \times 10^{-5}$M 2-mercaptoethanol. Cells were cultured in the presence of GM-CSF (1000 U/ml) and IL-4 (500 U/ml) for 4 days to become immature DCs. GM-CSF and IL-4 were added again along with fresh medium on day 3. The DC viability in cultures was assessed using the trypan blue exclusion protocol. Trypan blue-negative cells were considered alive. After culturing DCs from monocytes for 4-5 days, DCs were collected and transferred to 6 well plate ($1 \times 10^6$ cells/ml). Different concentrations of Lm-LLO or Lm-LLO-E6 or Lm-LLO-E7 were added to DCs culture (0, $10^7$, $10^8$, and $10^9$ CFU/ml) for an hour followed by adding gentamicin (50 ug/ml) to kill listeria, and cultured for 48 hr. DCs were stained with appropriate fluorescently labeled anti-PD-L1 antibody (PE anti-mouse PD-L1 and FITC anti-human PD-L1). Isotype-matched mAbs were used as negative controls. The stained cells were analyzed using FACSCalibur cytometer and CellQuest software (BD Biosciences).

3. Analysis of Antigen-Specific Cellular Immune Responses, Tregs, MDSC in Periphery and Tumors.

ELISPOT was used to detect IFNγ production in E6- or E7-restimulated (10 μg/ml) splenocyte cultures from treated and control mice, as suggested by the manufacturer (BD Biosciences, San Jose, Calif.). A CTL Immunospot Analyzer (Cellular Technology Ltd., Shaker Heights, Ohio) was used to analyze spots. The number of spots from irrelevant peptide (hgp 10025-33-KVPRNQDWL-Celtek Bioscience, Nashville, Tenn.) re-stimulated splenocytes were subtracted from E7-restimulated cultures. Tumor samples were processed using GentleMACS Dissociator and the solid tumor homogenization protocol, as suggested by the manufacturer (Miltenyi Biotec, Auburn, Calif.). The number of tumor-infiltrating CD8+, CD4+ Foxp3+ (Treg) and CD11b+Gr-1+ (MDSC) cells were analyzed within CD45+ hematopoietic cell population using flow cytometry assay as we described earlier. The level of Treg cells and MDSC was also evaluated in spleens of tumor-bearing treated and control mice using the same flow cytometry assay.

Example 3

The Expressions of E6 and PD-L1 are Positively Correlated in Lung Tumors and Are Associated With Poor Prognosis in NSCLC Patients We collected 122 surgically-resected lung tumors from NSCLC patients to examine whether E6 expression could be associated with PD-L1 expression. The data for E6 expression were obtained from previous studies. Immunohistochemistry analysis indicated that E6-positive lung tumors exhibited a higher frequency of positive PD-L1 expression (66.7% vs. 47.9%, P=0.039; FIG. 1). The PD-L1 expression was not associated with clinical parameters such as age, gender, smoking status, and stage, but it was associated with tumor histology, indicating that positive PD-L1 was expressed more frequently in adenocarcinoma than in squamous cell carcinoma (63.8% vs. 45.3, P=0.042).

Figure 2A:
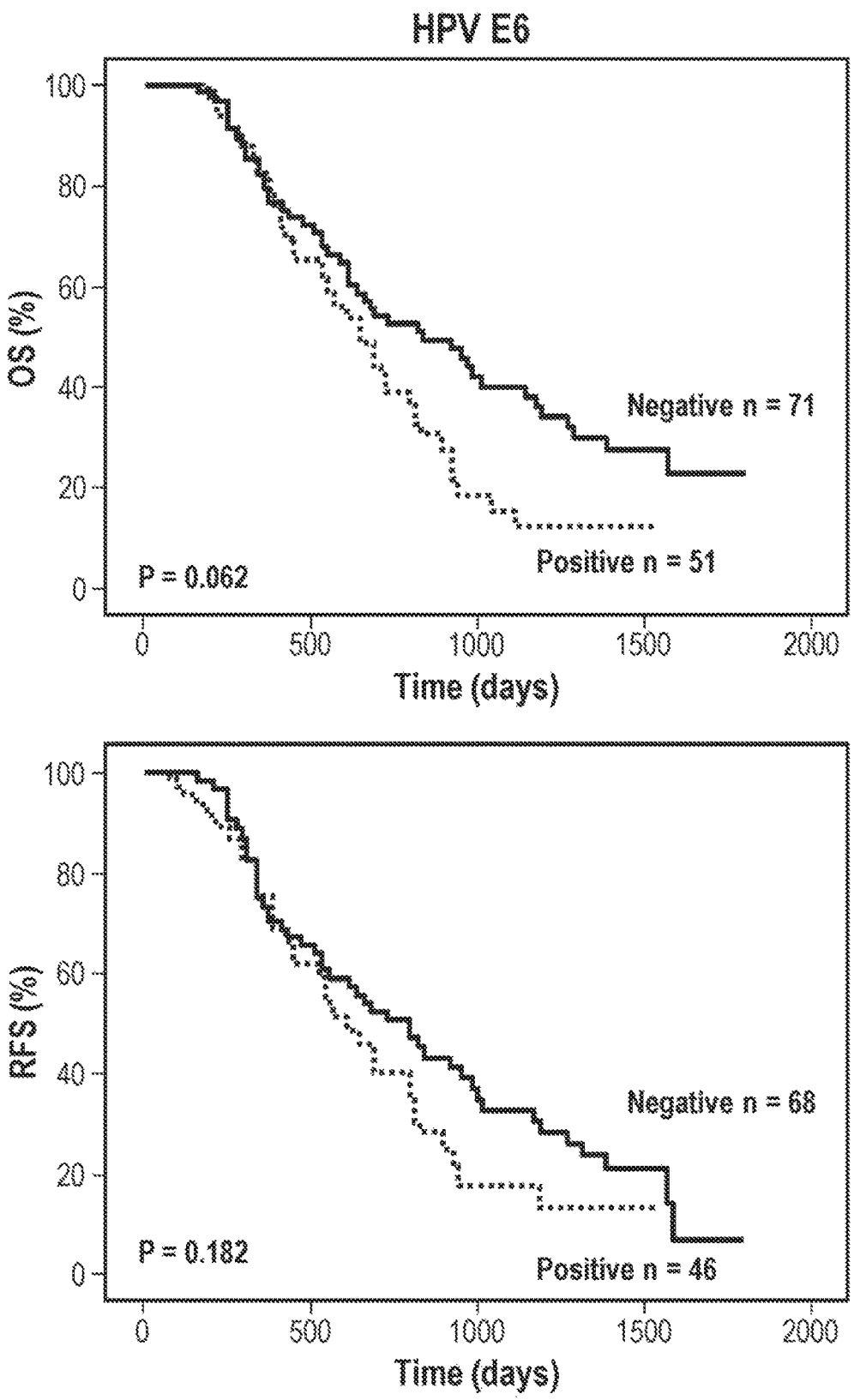
FIGS. 2A to C shows Kaplan-Meier survival analysis for assessing the influence of HPV16/18 E6 expression, PD-L1 expression, and a combination of both expressions on overall survival (OS) and relapse free survival (RFS) in NSCLC patients.
Figure 2B:
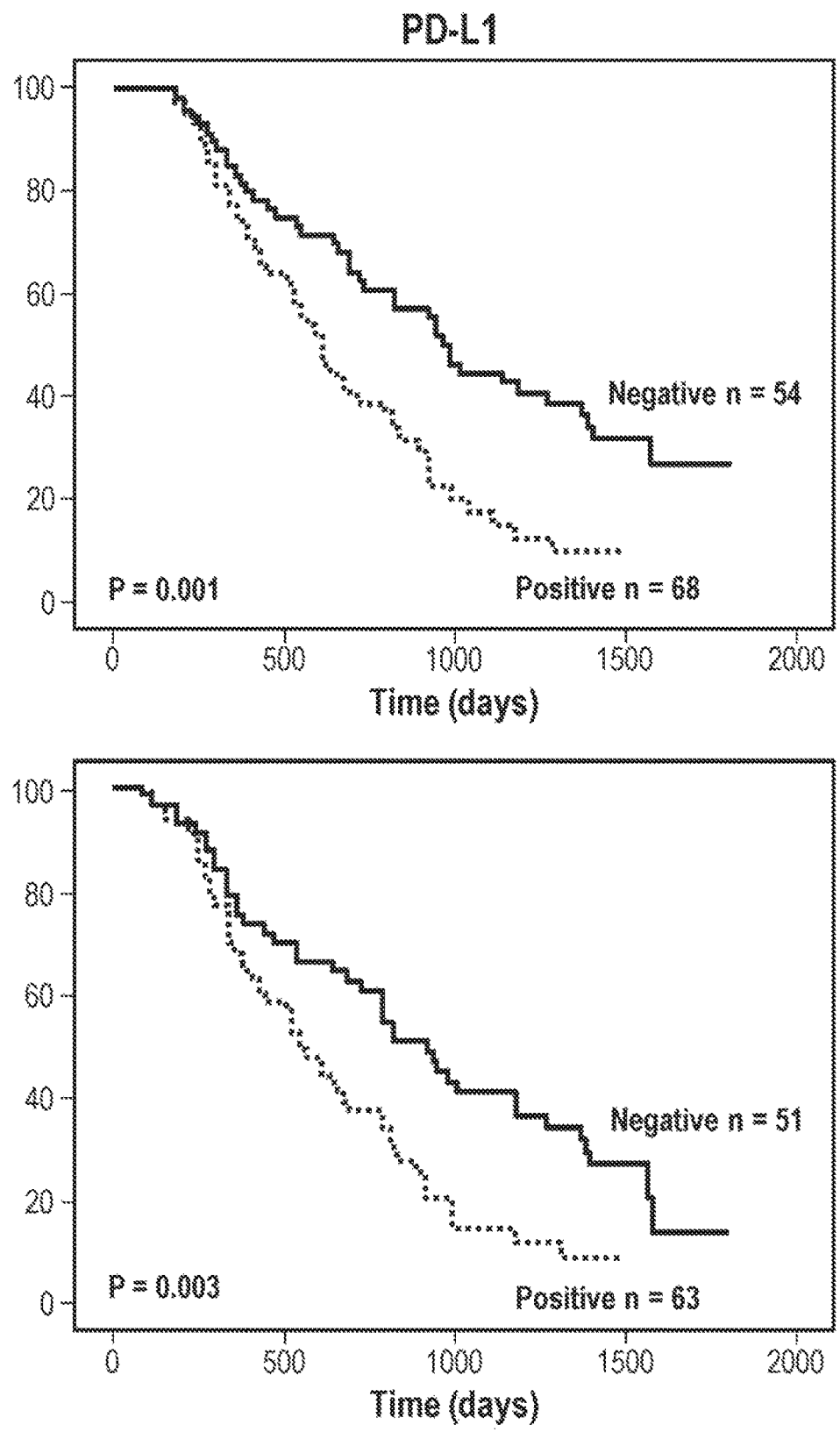
Figure 2C:
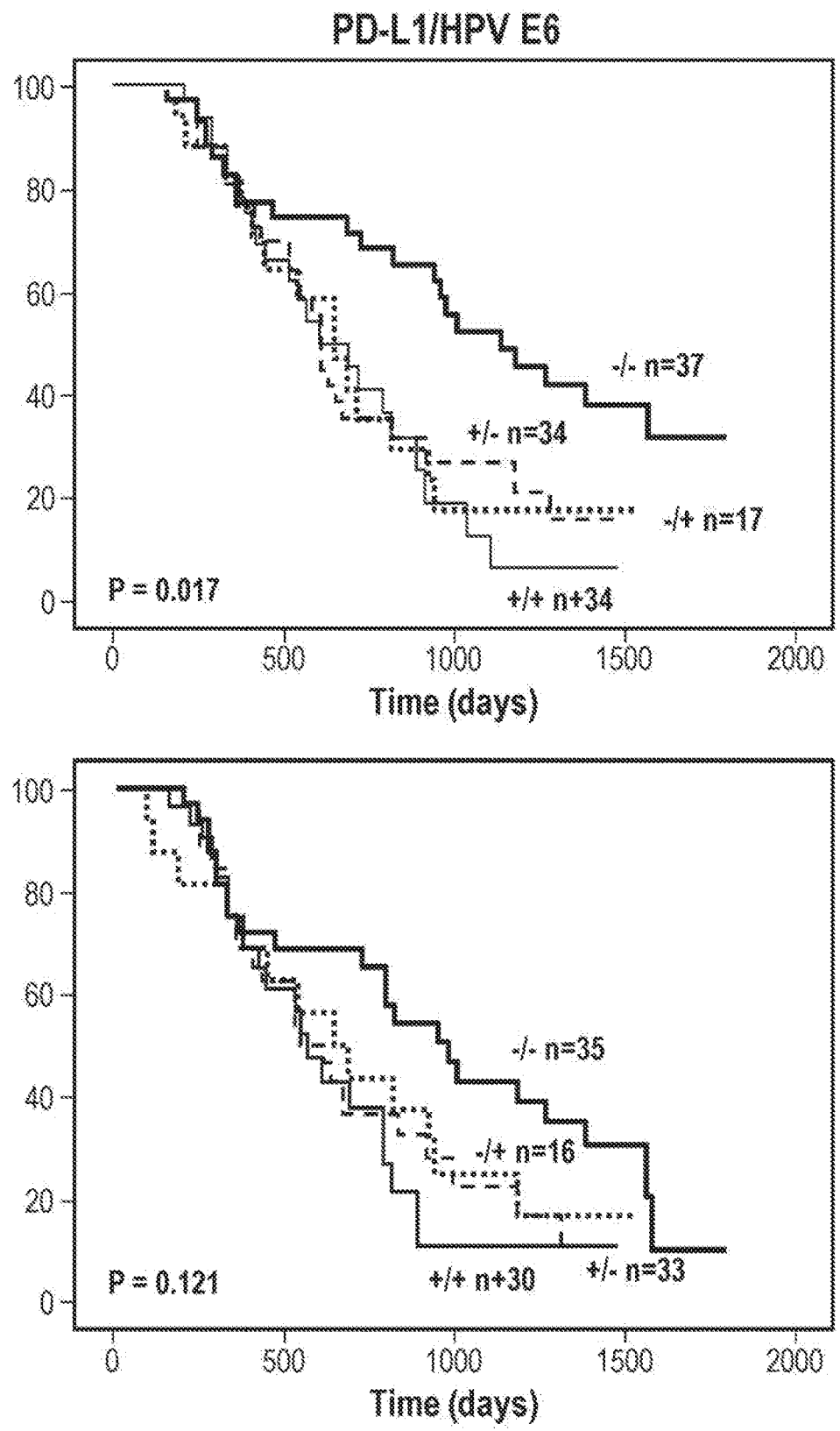

The possible association between E6 and PD-L1 expression, singly and combined, and overall survival (OS) and relapse free survival (RFS) was examined in NSCLC patients. Kaplan-Meier analysis showed that shorter OS and RFS were observed in patients with positive PD-L1 tumors than with negative PD-L1 tumors (P=0.001 for OS, P=0.003 for RFS; FIG. 2 B), but the E6 oncoprotein showed no prognostic value in this study population (FIG. 2A). However, the combination of PD-L1 and E6 expression had a prognostic value for OS, but not for RFS (P=0.017 for OS, P=0.121 for RFS; FIG. 2C). Cox-regression analysis further confirmed that patients with positive PD-L1 tumors had shorter OS and RFS periods when compared to patients with negative PD-L1 tumors (hazard ratio, HR, 1.69, 95% CI, 1.06-2.67, P=0.026 for OS; HR, 1.55, 95% CI, 0.97-2.48, P=0.045 for RFS; Table 1). The five-year survival percentage was lower in patients with positive PD-L1 tumors than with negative PD-L1 tumors (10.0 vs. 27.3% for OS, 8.6 vs. 13.3% for RFS; Table 1). However, the E6 oncoprotein showed no prognostic value in this study population. Interestingly, the PD-L1+/E6+ and PD-L1+/E6− combinations showed prognostic value for OS and RFS when the PD-L1−/E6− combination was used as the reference (Table 1). The lowest five-year survival percentage for OS and RFS was observed in patients with the PD-L1+/E6+ combination when compared with other three combinations (6.4% for OS, 5.7% for RFS; Table 1). These results suggest that PD-L1 expression may be used as an independent predictor of poor outcomes in HPV-infected NSCLC.

TABLE 1

Cox regression analysis HPV E6, PD-L1 status, and combining E6 with PD-L1 status on OS and RFS in NSCLC patients.

| | OS | | | | | | RFS | | | | | |
|---|---|---|---|---|---|---|---|---|---|---|---|---|
| | Patient No. | Median survival (month) | 5-year survival (%) | HR* | 95% CI | P | Patient No. | Median months | 5-year survival (%) | HR* | 95% CI | P |
| E6 protein | | | | | | | | | | | | |
| Negative | 71 | 27.4 | 23.0 | 1 | | | 68 | 24.4 | 7.1 | 1 | | |
| Positive | 51 | 21.5 | 12.3 | 1.49 | 0.95-2.32 | 0.080 | 46 | 19.0 | 13.4 | 1.28 | 0.80-2.03 | 0.302 |
| PD-L1 | | | | | | | | | | | | |
| Negative | 54 | 32.1 | 27.3 | 1 | | | 51 | 27.4 | 13.3 | 1 | | |
| Positive | 68 | 20.2 | 10.0 | 1.69 | 1.06-2.67 | 0.026 | 63 | 18.3 | 8.6 | 1.55 | 1.07-2.48 | 0.045 |
| PD-L1/HPV E6 | | | | | | | | | | | | |
| Negative/Negative | 37 | 34.1 | 31.8 | 1 | | | 35 | 31.6 | 10.2 | 1 | | |
| Negative/Positive | 17 | 21.5 | 17.6 | 1.89 | 0.84-3.81 | 0.076 | 16 | 21.5 | 16.7 | 1.45 | 0.71-2.99 | 0.312 |
| Positive/Negative | 34 | 20.3 | 16.1 | 2.00 | 1.08-3.71 | 0.027 | 33 | 18.3 | 11.2 | 1.71 | 0.93-3.15 | 0.086 |
| Positive/Positive | 34 | 19.0 | 6.4 | 2.30 | 1.23-4.30 | 0.009 | 30 | 18.3 | 5.7 | 1.90 | 0.99-3.65 | 0.053 |

*Adjusted for stage.

Example 4

Figure 3A:
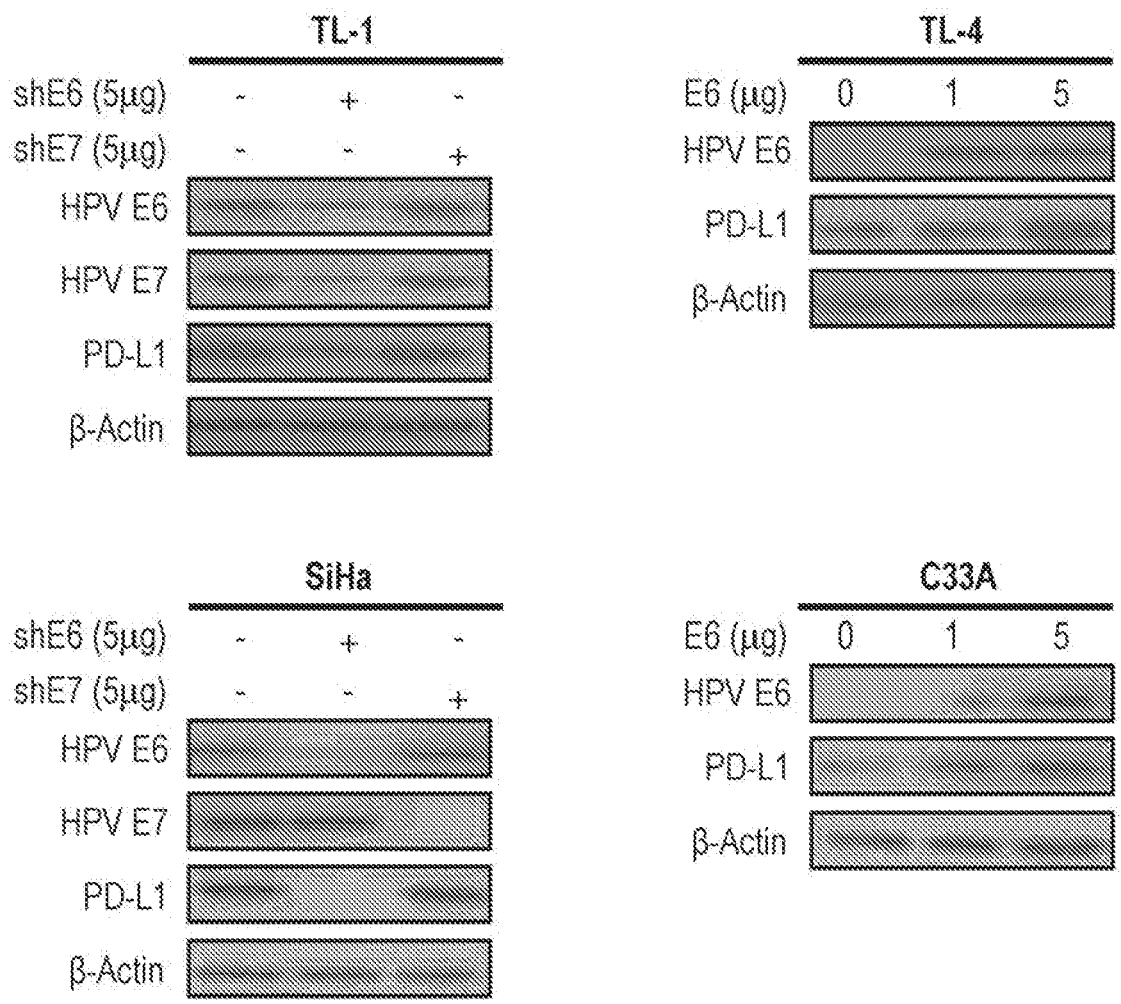
FIGS. 3A and B show that HPV16 E6-mediated PD-L1 expression may be responsible for colony formation and soft agar growth ability. (A) TL-1 and SiHa cells were transfected with E6 shRNA or E7 shRNA; TL-4 and C33A cells were transfected with an E6 expressing plasmid for 48 h. Western blotting analysis was performed to evaluate the expression of E6, E7, and PD-L1 in TL-1 and TL-4 cells. (B) TL-1 and SiHa cells were transfected with E6 shRNA and PD-L1 expressing plasmid; TL-4 and C33A cells were transfected with E6 expressing plasmid and PD-L1 shRNA for 48 h. The colony formation ability was evaluated after 7 days. The soft agar growth ability was determined after 14 days.

The E6 Oncoprotein Increases PD-L1 Expression to Promote Colony Formation and Soft Agar Growth in HPV-Infected Lung Cancer Cells We examined the possibility that E6 oncoprotein expression could increase PD-L1 expression to promote colony formation and soft agar growth in HPV-infected lung cancer cells. HPV16-positive TL-1 cells were collected for transfection with E6 or E7 small hairpin (sh)RNA and for comparison with HPV16-negative TL-4 cells transfected with the E6 or E7 expression vector. This comparison would verify whether the E6, but not the E7 oncoprotein, is responsible for PD-L1 expression in lung cancer cells (FIG. 3A). Western blotting indicated that E6 and E7 protein expressions were decreased and increased as expected by E6 or E7 manipulation (FIG. 3A). Interestingly, PD-L1 expression was markedly decreased by E6 knockdown in TL-1 cells, but was increased by E6 overexpression in TL-4 cells (FIG. 3A). The PD-L1 expression was unchanged by E7 manipulation in both cell types (FIG. 3A). Similar responses were seen in the HPV16-positive and HPV16-negative cervical SiHa and C33A cells subjected to the same treatments (FIG. 3A). These results suggest that the E6, but not the E7, oncoprotein may be responsible for PD-L1 expression in HPV-infected lung cancer cells.

Figure 3B:
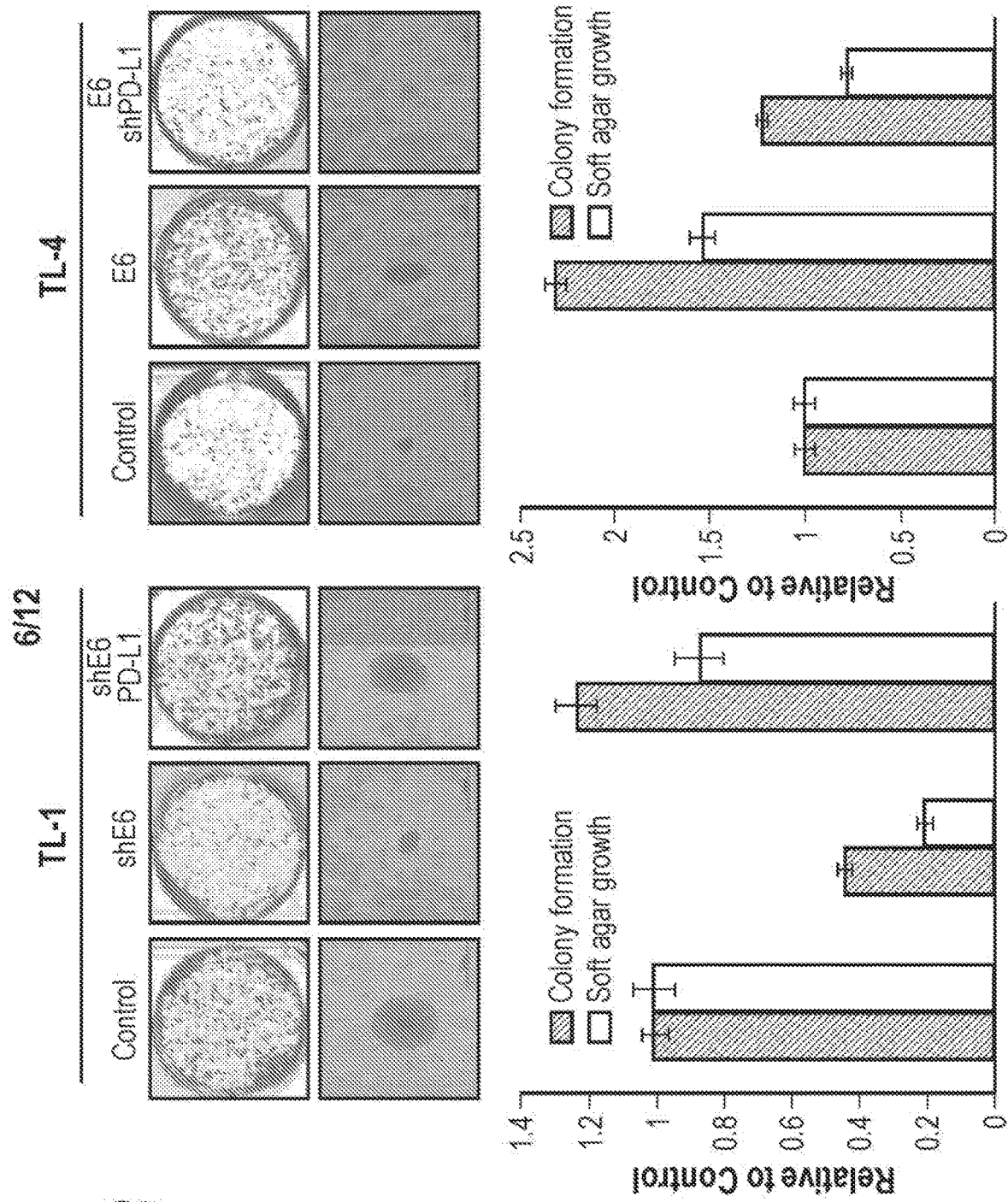
Figure 3B:
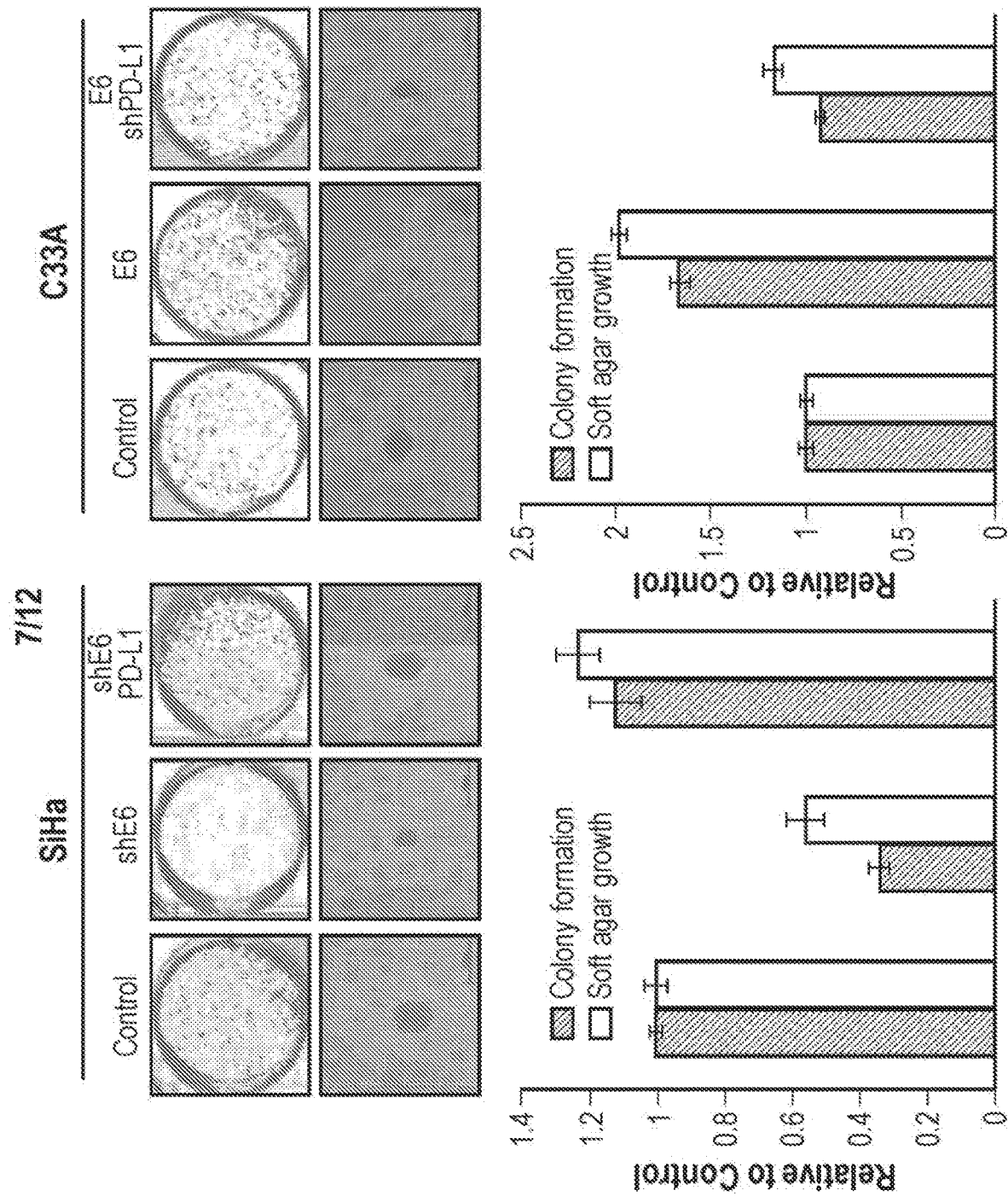

We next examined whether manipulation of PD-L1 expression by E6 could attenuate the abilities for colony formation and soft agar growth in lung cancer cells. The representative colony growth in agar plates and soft agar growth colonies in soft agar plates are shown in FIG. 2B (upper panel). The abilities of colony formation and soft agar growth were markedly decreased by E6 knockdown in TL-1 cells, but both abilities were significantly increased by E6 overexpression in TL-4 cells (FIG. 3B). However, the increase in the colony formation and soft agar growth ability by E6 oncoprotein was almost completely rescued by PD-L1 knockdown in TL-4 cells (FIG. 2B). Similar findings were observed in SiHa and C33A cervical cancer cells subjected to the same treatments (FIG. 3B). These results clearly indicate that E6-mediated PD-L1 expression may be responsible for colony formation and soft agar growth in HPV-infected lung cancer cells.

Example 5

Figure 4A:
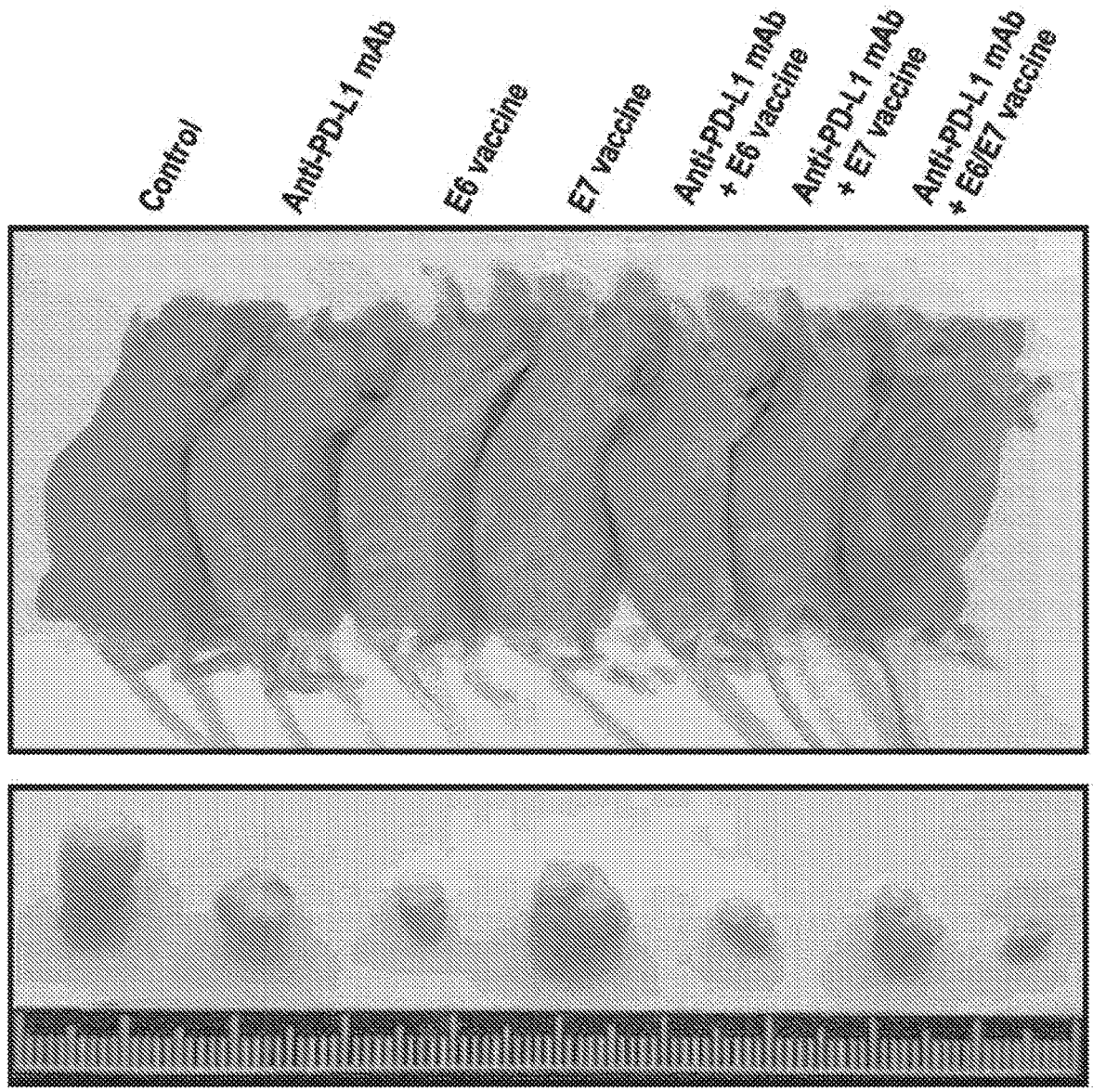
FIGS. 4A and B show the combination of Lm-LLO-E6 vaccine+anti-PD-L1 mAb resulted in stronger suppression of subcutaneous tumor growth in nude mice. The nude mice were subcutaneously injected with HPV16-infected TL-1 cells that expressed E6 and E7 oncoprotein. After 7 days, the mice were treated with anti-PD-L1 mAb (25m/mouse), Lm-LLO-E6 (E6) vaccine ($5 \times 10^6$ CFU/mouse), Lm-LLO-E7 (E7) vaccine ($5 \times 10^6$ CFU/mouse) or a combination of antibody plus one or both vaccines by peritoneal injection. The representative tumor burdens in the 7 groups are illustrated. The tumor volume in the nude mice of each group was measured at 7-day intervals from Day 0 to Day 70. Mean±S.E.M. values ($cm^3$) were calculated from the tumor volumes of five nude mice in each group.
Figure 4B:
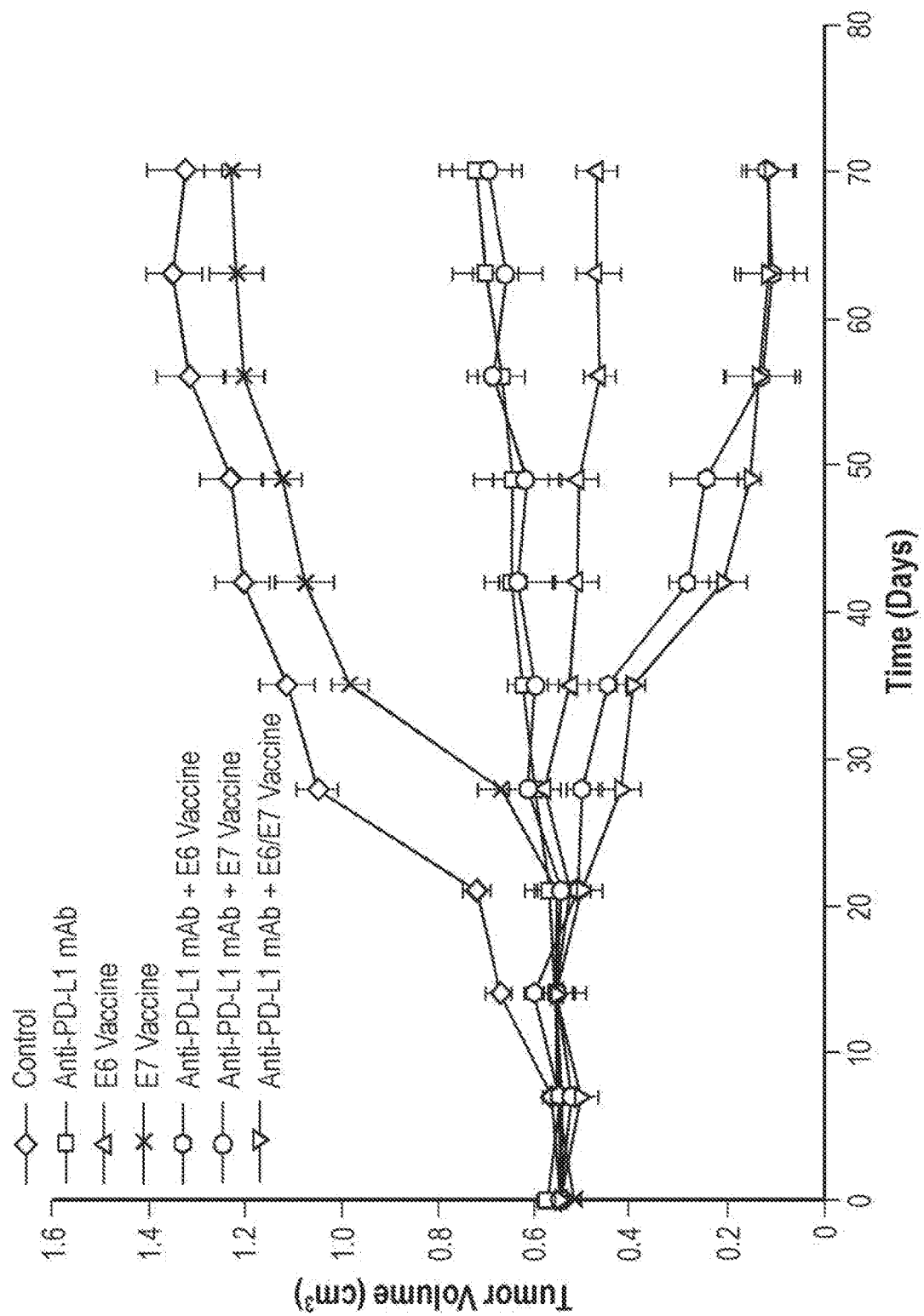

The Anti-PD-L1 mAb+Lm-LLO-E6 Vaccine Almost Completely Suppresses Subcutaneous Tumor Growth Induced by TL-1 Cells in Nude Mice The anti-PD-L1 mAb may provide durable tumor suppression and a clinical benefit in advanced NSCLC (15). The finding that PD-L1 may be responsible for E6-mediated colony formation and soft agar growth in HPV-infected lung cancer (FIGS. 2A thru 2C), therefore suggested that the anti-PD-L1 mAb+Lm-LLO-E6 vaccine combination might have superior suppressive effects on tumor growth induced by TL-1 cells in nude mice. The nude mice were randomly divided into seven groups of five nude mice each, which were injected with TL-1 cells and then treated with either anti-PD-L 1 mAb, Lm-LLO-E6 vaccine, Lm-LLO-E7 vaccine, anti-PD-L1 mAb+Lm-LLO-E6 vaccine, anti-PD-L 1 mAb+Lm-LLO-E7 vaccine, or anti-PD-L1 mAb+Lm-LLO-E6/E7 vaccine. The control group mice were treated with TL-1 cells only. The representative tumor burdens in each group are shown in FIGS. 4A and 4B. The subcutaneous tumor burdens induced by TL-1 cells were almost completely suppressed by anti-PD-L1 mAb+Lm-LLO-E6 vaccine or anti-PD-L 1 mAb+Lm-LLO-E6/E7 vaccine when compared with the control group. However, a higher anti-tumor activity was observed in the Lm-LLO-E6 vaccine group than in the anti-PD-L1 mAb or the anti-PD-L1+Lm-LLO-E7 vaccine groups. The tumors induced by TL-1 cells were nearly unchanged by Lm-LLO-E7 vaccine treatment (FIGS. 4A and 4B). These results supported the findings of the cell models, indicating that PD-L1 may be responsible for E6-mediated tumor growth and metastasis in HPV-infected cancers.

Example 6

Figure 5A:
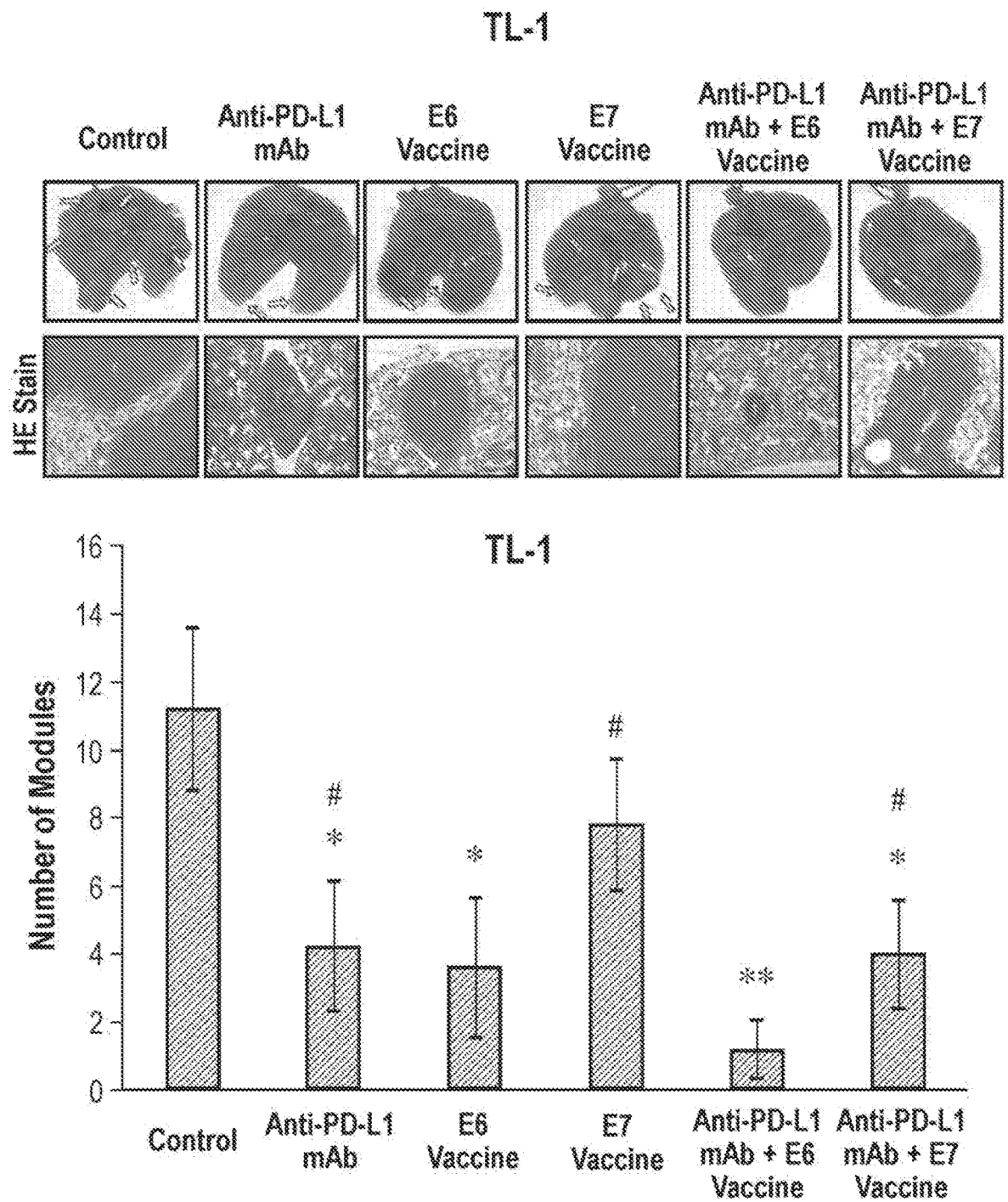
FIGS. 5A and B show that metastatic lung tumor nodules induced by TL-1 and SiHa cells in nude mice were efficiently suppressed by combined anti-PD-L1 mAb+Lm-LLO-E6 vaccine therapy. The nude mice were intravenously injected with HPV16-infected (A) TL-1 cells or (B) SiHa cells. After 14 days, the mice were treated with anti-PD-L1 mAb (25m/mouse), Lm-LLO-E6 (E6) vaccine ($5 \times 10^6$ CFU/mouse), Lm-LLO-E7 (E7) vaccine ($5 \times 10^6$ CFU/mouse) or combinations of antibody and vaccine by peritoneal injection. Representative H & E staining is shown for the lung tumor nodules from each group of mice. The number of lung tumor nodules in each group of mice is also shown. Data represent means±SD. The P value was statistically determined by the Student's t-test. * $P<0.05$, compare with control; ** $P<0.001$, compared with control; # $P<0.05$ compared with Anti-PD-L1 mAb+Lm-LLO-E6 vaccine.
Figure 5B:
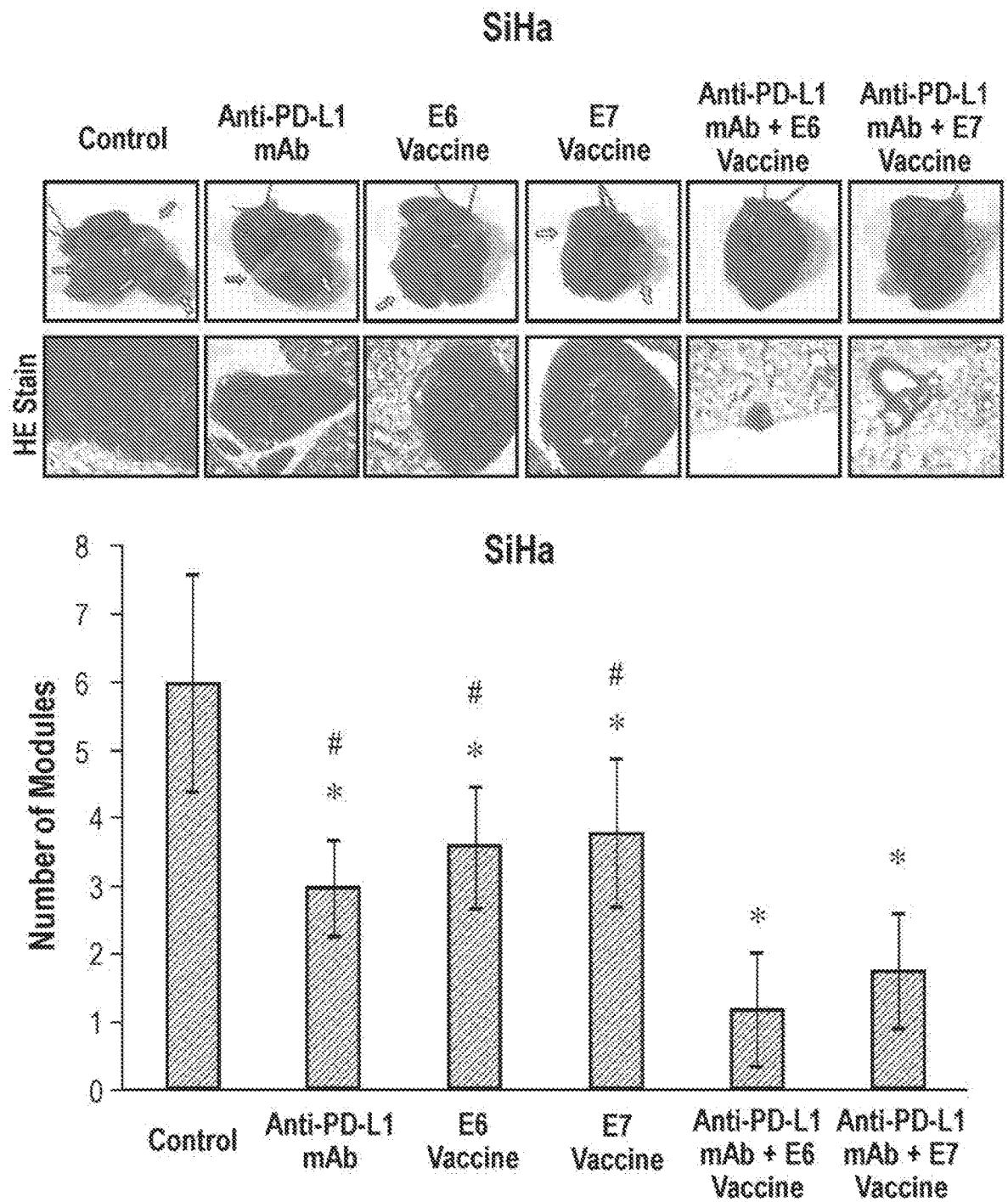

Metastatic Lung Tumor Nodules Induced by TL-1 Cells in Nude Mice Are Efficiently Suppressed by Anti-PD-L1 mAb+Lm-LLO-E6 Vaccine Combination Therapy We also used a tail-vein animal model to verify whether the anti-PD-L1 mAb+Lm-LLO-E6 combination can suppress metastatic lung tumor nodule formation induced by TL-1 cells in nude mice. The experiments were halted at 77 days. The representative metastatic lung tumor nodules induced by TL-1 cells in each group were compared with those induced by SiHa cells. Tumors were confirmed by H & E staining (FIG. 5A). Representative immunostaining results for the lung tumor nodules of each group indicated a significant suppression of PD-L1 and E6 expression in these lung tumor nodules by anti-PD-L1 mAb and Lm-LLO-E6 vaccine when compared with the control group. The number of metastatic lung tumor nodules induced by TL-1 cells was most suppressed by the anti-PD-L1 mAb+Lm-LLO-E6 vaccine, followed by E6 vaccine, anti-PD-L1 mAb, anti-PD-L1+Lm-LLO-E7 vaccine, and Lm-LLO-E7 vaccine when compared with the control group (FIG. 5A). Similar findings were observed in metastatic lung tumor nodules induced by SiHa cells in nude mice subjected to the same treatments (FIG. 5B).

Figure 6:
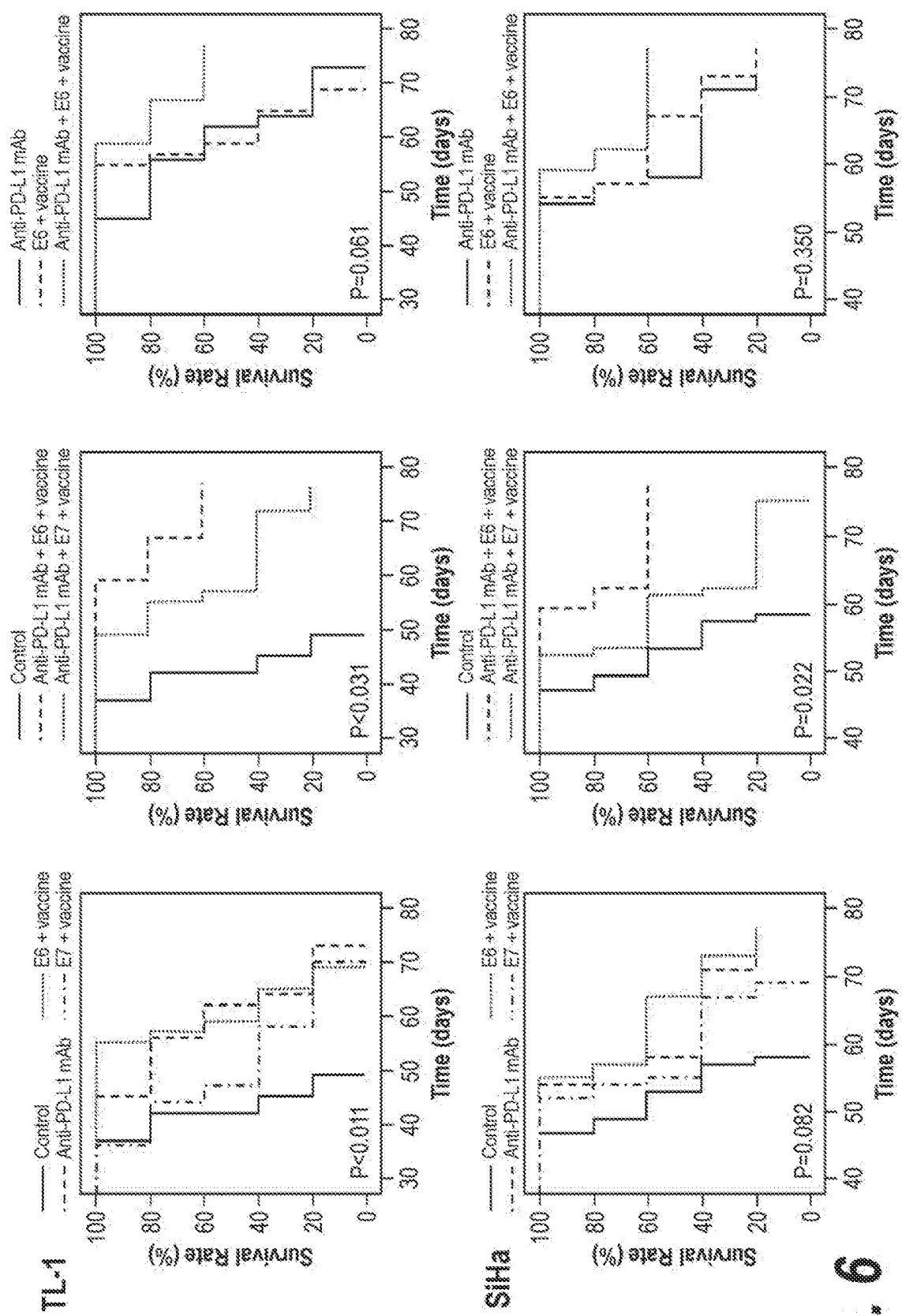
FIG. 6 shows Kaplan-Meier analysis for assessing the influence of PD-L1 mAb, Lm-LLO-E6 (E6) vaccine, Lm-LLO-E7 (E7) vaccine, the combination of PD-L1 mAb+Lm-LLO-E6 vaccine, and the combination of PD-L1 mAb+Lm-LLO-E7 vaccine on the survival of mice injected with TL-1 or SiHa cells. The final day of the experiment was day 77.

The body weights of the control mice injected with TL-1 cells were significantly lower than those of mice injected with anti-PD-L1 mAb, Lm-LLO-E6 vaccine, anti-PD-L1 mAb+Lm-LLO-E6 vaccine, and anti-PD-L1 mAb+Lm-LLO-E7 vaccine, but they did not differ from those that received Lm-LLO-E7 vaccine treatment. Similar observations were made for the body weights of mice injected with SiHa cells subjected to the same treatments. The survival days of the nude mice injected with TL-1 or SiHa cells were significantly prolonged by the anti-PD-L1 mAb+Lm-LLO-E6 vaccine combination when compared with the control group (FIG. 6). Three of five mice were alive at 77 days in the anti-PD-L1 mAb+Lm-LLO-E6 vaccine and the anti-PD-L1 mAb+Lm-LLO-E7 vaccine groups treated with TL-1 and SiHa cells. The last mouse died at 49 and 58 days, respectively, in the control groups treated with TL-1 and SiHa cells. The survival days of the nude mice injected with TL-1 cells were significantly prolonged with the anti-PD-L1 mAb+Lm-LLO-E6 vaccine when compared with the anti-PD-L1 mAb+Lm-LLO-E7 vaccine, Lm-LLO-E6 vaccine or anti-PD-L1 mAb (P=0.004 for anti-PD-L1 mAb+Lm-LLO-E7 vaccine, P=0.037 for Lm-LLO-E6 vaccine, P=0.043 for anti-PD-L1 mAb, FIG. 6). These results suggest that the anti-PD-L1 mAb+Lm-LLO-E6 vaccine has the greatest potential to suppress metastatic lung tumor nodule formation in HPV-infected lung and cervical cancer and, consequently, to prolong the survival of these mice.

What is claimed is:

1. A pharmaceutical combination, comprising an anti-PD-L1 antibody or anti-PD-1 antibody in combination with a HPV antigen-associated vaccine, wherein the HPV antigen-associated vaccine is a vector expressing LLO-E6 fusion protein, LLO-E6-E7 fusion protein, ADXS-HPV, or combinations thereof.

2. The pharmaceutical combination of claim 1, wherein the anti-PD-L1 antibody or anti-PD-1 antibody is an amount ranging from 5 to about 50 mg/mL and the HPV antigen-associated vaccine is in an amount ranging from about $1 \times 10^4$ to about $1 \times 10^{12}$ CFU/dose.

3. The pharmaceutical combination of claim 1, wherein the anti-PD-L1 antibody is atezolizumab or MEDI4736 and the anti-PD-1 antibody is nivolumab or pembrolizumab.

4. The pharmaceutical combination of claim 1, wherein the HPV-associated vaccine is a vector carrying LLO-E6 fusion protein.

5. The pharmaceutical combination of claim 1, wherein the vector carrying LLO-E6 fusion protein or LLO-E6-E7 fusion protein is a *Listeria* carrying plasmid expressing LLO-E6 fusion protein or LLO-E6-E7 fusion protein.

6. The pharmaceutical combination of claim 5, wherein the *Listeria* is *Listeria monocytogenes*.

7. The pharmaceutical combination of claim 1, which further comprises a second anticancer agent.

8. A method for treating and/or preventing a tumor growth, invasion and/or metastasis in a subject suffering from a PD-L1+/E6+, PD-L1+/E7+ or PD-L1/E6$^+$/E7$^+$ tumor, comprising administering a pharmaceutical composition comprising an anti-PD-L1 antibody or anti-PD-1 antibody and a HPV antigen-associated vaccine, wherein the HPV antigen-associated vaccine is a vector expressing LLO-E6 fusion protein, LLO-E6-E7 fusion protein, ADXS-HPV, or combinations thereof.

9. The method of claim 8, wherein the PD-L1+/E6+, PD-L1+/E7+ or PD-L1$^+$/E6$^+$/E7$^+$ tumor is lung tumor, cervical tumor, vagina tumor, vulva tumor, penis tumor, anus tumor, rectum tumor, melanoma, non-small cell lung cancer (NSCLC), head and neck squamous cell carcinoma (HNSCC) and oropharynx tumor.

10. The method of claim 9, wherein the lung tumor is non-small cell lung cancer.

11. The method of claim 8, wherein the PD-L1+/E6+, PD-L1+/E7+ or PD-L1$^+$/E6$^+$/E7$^+$ tumor is HPV-infected lung or cervical tumor.

12. The method of claim 8, wherein the anti-PD-L1 antibody is atezolizumab or MEDI4736 and the anti-PD-1 antibody is nivolumab or pembrolizumab.

13. The method of claim 8, wherein the anti-PD-L1 antibody or anti-PD-1 antibody is in a dosing amount ranging from about 0.01 mg/kg to about 20 mg/kg.

14. The method of claim 8, wherein the HPV antigen-associated vaccine is in a dosing amount ranging from about $1 \times 10^4$ to about $1 \times 10^{12}$ CFU/dose.

15. The method of claim 8, wherein the anti-PD-L1 antibody or anti-PD-1 antibody and the HPV antigen-associated vaccine are administered simultaneously, concurrently, separately or sequentially.

16. A method for improving a PD-1/PD-L1 cancer immunotherapy in a subject having a PD-L1+/E6+, PD-L1+/E7+ or PD-L1/E6$^+$/E7$^+$ tumor, comprising administering a pharmaceutical composition comprising an anti-PD-L1 antibody or anti-PD-1 antibody in combination with a HPV antigen-associated vaccine, wherein the HPV antigen-associated vaccine is a vector expressing LLO-E6 fusion protein, LLO-E6-E7 fusion protein, ADXS-HPV, or combinations thereof.

17. The method of claim 16, wherein the cancer prognosis is improved.

18. The method of claim 16, wherein the anti-PD-L1 antibody or anti-PD-1 antibody and the HPV antigen-associated vaccine are administered simultaneously, concurrently, separately or sequentially.

* * * * *

SEQUENCE LISTING

<160> NUMBER OF SEQ ID NOS: 14

<210> SEQ ID NO 1
<211> LENGTH: 1803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaagaaaca cgcggatgaa      180
atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa aataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540
gcagtaaata cattagtgga agatggaat gaaaaatatg ctcaagctta tccaaatgta      600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta caagaccttc cagatttttc ggcaaagctg ttactaaaga gcagttgcaa     840
gcgcttggag tgaatgcaga aaatcctcct gcatatatct caagtgtggc gtatggccgt     900
caagtttatt tgaaattatc aactaattcc catagtacta agtaaaagc tgcttttgat      960
gctgccgtaa gcggaaaatc tgtctcaggt gatgtagaac taacaaatat catcaaaaat    1020
tcttccttca aagccgtaat ttacggaggt tccgcaaaag atgaagttca atcatcgac     1080
ggcaacctcg agacttacg cgatattttg aaaaaggcg ctacttttaa tcgagaaaca     1140
ccaggagttc ccattgctta caacaaac ttcctaaaag acaatgaatt agctgttatt      1200
aaaaacaact cagaatatat tgaaacaact tcaaaagctt atacagatgg aaaaattaac    1260
atcgatcact ctggaggata cgttgctcaa ttcaacattt cttgggatga agtaaattat    1320
gatctcgagc accaaaagag aactgcaatg tttcaggacc cacaggagcg acccagaaag    1380
ttaccacagt tatgcacaga gctgcaaaca actatacatg atataatatt agaatgtgtg    1440
tactgcaagc aacagttact gcgacgtgag gtatatgact ttgcttttcg ggatttatgc    1500
atagtatata gagatgggaa tccatatgct gtatgtgata atgtttaaa gttttattct    1560
aaaattagtg agtatagaca ttattgttat agtttgtatg gaacaacatt agaacagcaa    1620
tacaacaaac cgttgtgtga tttgttaatt aggtgtatta actgtcaaaa gccactgtgt    1680
cctgaagaaa agcaaagaca tctggacaaa aagcaaagat tccataatat aagggggtcgg   1740
tggaccggtc gatgtatgtc ttgttgcaga tcatcaagaa cacgtagaga aacccagctg   1800
taa                                                                  1803
```

<210> SEQ ID NO 2
<211> LENGTH: 600
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
```

20                  25                  30
Glu Asn Ser Ile Ser Ser Met Ala Pro Pro Ala Ser Pro Ala Ser
                35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
                115                 120                 125

Ala Leu Val Lys Ala Asn Ser Glu Leu Val Glu Asn Gln Pro Asp Val
                130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Pro Asn Val Ser Ala Lys Ile Asp Tyr Asp Asp
                195                 200                 205

Glu Met Ala Tyr Ser Glu Ser Gln Leu Ile Ala Lys Phe Gly Thr Ala
                210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
                275                 280                 285

Pro Pro Ala Tyr Ile Ser Ser Val Ala Tyr Gly Arg Gln Val Tyr Leu
                290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
                370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp Leu Glu His Gln Lys Arg Thr
                435                 440                 445

```
Ala Met Phe Gln Asp Pro Gln Glu Arg Pro Arg Lys Leu Pro Gln Leu
    450                 455                 460

Cys Thr Glu Leu Gln Thr Thr Ile His Asp Ile Ile Leu Glu Cys Val
465                 470                 475                 480

Tyr Cys Lys Gln Gln Leu Leu Arg Arg Glu Val Tyr Asp Phe Ala Phe
                485                 490                 495

Arg Asp Leu Cys Ile Val Tyr Arg Asp Gly Asn Pro Tyr Ala Val Cys
                500                 505                 510

Asp Lys Cys Leu Lys Phe Tyr Ser Lys Ile Ser Glu Tyr Arg His Tyr
                515                 520                 525

Cys Tyr Ser Leu Tyr Gly Thr Thr Leu Glu Gln Gln Tyr Asn Lys Pro
    530                 535                 540

Leu Cys Asp Leu Leu Ile Arg Cys Ile Asn Cys Gln Lys Pro Leu Cys
545                 550                 555                 560

Pro Glu Glu Lys Gln Arg His Leu Asp Lys Lys Gln Arg Phe His Asn
                565                 570                 575

Ile Arg Gly Arg Trp Thr Gly Arg Cys Met Ser Cys Cys Arg Ser Ser
                580                 585                 590

Arg Thr Arg Arg Glu Thr Gln Leu
                595                 600

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggctcgagca tggagataca cc                                              22

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggactagt ttatggtttc tgagaaca                                        28
```

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gggggctagc cctcctttga ttagtatatt c        31

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ctccctcgag atcataattt acttcatc        28

<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gactacaagg acgatgaccg acaagtgata acccgggatc taaataaatc cgttt        55

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
cccgtcgaca gctcttcttg gtgaag        26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcggatccca tggagataca cctac        25

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gctctagatt atggtttctg ag        22

<210> SEQ ID NO 14

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Val Pro Arg Asn Gln Asp Trp Leu
1               5
```